United States Patent
Dandliker et al.

[19]

[11] Patent Number: 5,876,672
[45] Date of Patent: *Mar. 2, 1999

[54] TRANSIENT STATE LUMINESCENE ASSAY APPARATUS

[75] Inventors: Walter Beach Dandliker; June K. Dandliker, both of La Jolla, Calif.; Jacques Claude Levin, Fort Lauderdale, Fla.

[73] Assignee: Diatron Diagnostics Corporation, San Deigo, Calif.

[ * ] Notice: The portion of the term of this patent subsequent to Apr. 12, 2011, has been disclaimed.

[21] Appl. No.: 655,963

[22] Filed: May 31, 1996

Related U.S. Application Data

[63] Continuation of Ser. No. 196,594, Feb. 9, 1994, abandoned, which is a continuation of Ser. No. 490,770, Mar. 6, 1990, Pat. No. 5,302,349, which is a continuation-in-part of Ser. No. 365,420, Jun. 13, 1989, abandoned.

[51] Int. Cl.$^6$ .................................................... G01N 21/64
[52] U.S. Cl. ....................... 422/82.08; 436/546; 436/172; 356/307; 356/317; 250/458.1
[58] Field of Search .................................. 422/82.08, 52; 250/458.1, 459.1, 461.1, 461.2; 356/317, 318, 307, 417; 456/536, 546, 172

[56] References Cited

U.S. PATENT DOCUMENTS

| | | | |
|---|---|---|---|
| 4,131,800 | 12/1978 | Bruck et al. | 250/461.2 |
| 4,341,957 | 7/1982 | Wieder | 250/302 |
| 4,419,583 | 12/1983 | Noeller | 356/417 |
| 4,555,177 | 11/1985 | Barrett | 250/459.1 |
| 4,786,170 | 11/1988 | Groebler | 356/417 |
| 4,877,965 | 11/1989 | Dandliker et al. | 250/461.2 |

*Primary Examiner*—Jeffrey Snay
*Attorney, Agent, or Firm*—Ellsworth R. Roston; Fulwider Patton Lee & Utecht, LLP

[57] ABSTRACT

Light, pulsed or continuous at a wavelength (e.g. 780 nm), fluoresceces a specimen. The specimens may be combinations of a dye (preferably labelled), an antigen (e.g. rubella) and an antibody reactive with the antigen, with properties of polarizing the light when fluoresced. The light polarized in a first direction (e.g. z-axis) parallel to the incident light and in a second direction (e.g. x-axis) perpendicular to the incident light are measured. A second specimen is then provided with the antigen and the antibody but without the dye. The same light as discussed above fluoresces the second specimen and polarizes the light when fluoresced. The light polarized in the first (z-axis) and second (x-axis) directions in the second specimen is measured. These measurements are processed in a microprocessor with the measurements in the z and x directions in the first specimen to identify the antigen or, when the antigen is known, to identify the concentration of the antigen in the first specimen. When the light is pulsed, the measurements are made in a time window beginning after the initiation, and terminating before the end, of the fluorescence of the combination of the dye, the antibody and the antigen. When the light is continuous, it is modulated. Measurements are made of the phase shifts in the polarized light in the z and x directions as a result of the light modulations.

15 Claims, 3 Drawing Sheets

TRANSIENT STATE LUMINESCENE ASSAY APPARATUS

This is a continuation of application Ser. No. 08/196,594 filed Feb. 9, 1994, now abandoned, which is a continuation of Ser. No. 07/490,770 filed Mar. 6, 1990, now U.S. Pat. No. 5,302,249, which in turn is a continuation-in-part of application Ser. No. 07/365,420 filed Jun. 13, 1989 (now abandoned), by Walter B. Dandliker, June K. Dandliker and Jacques Claude Levin for "Transient State Luminescence Assays" and assigned of record to the assignee of record of this application.

This invention relates to fluorometers for detecting a particular specimen in a solution. More particularly, the invention relates to a fluorometer for obtaining sensitive and reliable measurements of a particular fluorescence from a specimen by providing a polarization of the fluorescence and measuring such polarization. The invention also includes apparatus for eliminating the effects of noise from such measurements. The invention also relates to methods of obtaining sensitive and reliable measurements of a particular fluorescence from a specimen by such polarization techniques.

In general, prior art fluorometers suffer from a common problem of being unable to discriminate between the generated fluorescent signal and the background noise. Certain types of conventional fluorometers discriminate between the fluorescent signal and the background noise on the basis of wavelength. This type of discrimination is generally not sufficient for many types of fluorescent signals.

Another type of discrimination can be accomplished using a time-gaged technique. In particular, these instruments are based on the principle of permitting the observation of the fluorescence or luminescence a short, and if desired a variable, time after the excitation period. Time gaged fluorometers therefore add an additional level of discrimination by viewing the signal fluorescence during an optimal time window. In the past, this technique generally employed a fluorophore of long decay time in order to allow the background fluorescence to delay. The long delay times produced relatively slow measurements and lost information afforded by the polarization. Furthermore, the measurements were clouded because they contained a considerable amount of background noise.

The time gaged technique is in general based on a phosphoroscope invented by Becquerel in 1867. In the Becquerel instrument, the luminescent substance is placed between two rotating discs which are mounted on a common axis and which have sector shaped apertures. The variable time gaging is achieved by an adjustment of the angle between a sector on one disc and a sector on the other. Subsequent refinements of the time gaging technique have been accomplished by the use of spark discharges, oscilloscopes, Kerr cells, supersonic cells and lasers.

The rotating disc invented by Becquerel was put into a conical configuration for a microscope by Jones as described in U.S. Pat. No. 2,071,408 in 1937. Other more recent improvements have used electronic techniques. For example, U.S. Pat. No. 4,341,957 to Wieder provided for the gaging of a detecting circuit electronically and used a laser for excitation. In this way, as in other refinements of the Becquerel phosphoroscope, the gaging mechanism may be adjusted so that observation of the desired signal can be optimized within the limits of the phosphoroscope. Other prior art devices such as U.S. Pat. No. 4,006,360 to Mueller use electronic gaging to distinguish between species of differing decay times where two species are involved and one is a bound dye and the other is an unbound dye.

Several commercial instruments are currently available for the measurement of decay times or lifetimes. These instruments utilize nanosecond flash sources (electric spark in air at reduced pressure). One instrument introduces the output of a photomultiplier tube to a fast oscilloscope. Provision is made to match the experimental curve with a sum to 3 or 4 exponentials.

A second instrument excites the sample by repeated flashes from the source (such as at 5 kHz) and pulses the photomultiplier at progressively increased times after each flash. The output is fed into a recorder or computer to provide an intensity vs. time signal. In addition, this instrument is supplied with software to reconvolute the experimental curve by a well known method termed Linearized Least Squares Reconvolution.

A third instrument utilizes a flash source (typically at 1 kHz). A timer is started at the time of the flash and stopped when the photomultiplier detects a photon from the sample. Subsequently, counts are accumulated in a series of time boxes giving a relationship leading to the decay curve for the fluorescence.

Both wavelength-based discrimination and time-based discrimination suffer by having background fluorescence superimposed on the signal with only an indirect means of segregating the background fluorescence from the signal. In addition, the use of dyes of long decay time effectively smears the desired signal over a long time period, thus making this signal hard to extract. Dyes of long decay time have inherently low extinction coefficients and therefore provide inefficient excitation of the fluorescence.

In co-pending application Ser. No. 751,746 now U.S. Pat. No. 4,827,7965, filed and assigned of record to the assignee of record by Walter B. Dandliker on Jul. 1, 1985, for a "Fluorometer" of this application, a new type of fluorometer is disclosed and claimed which permits the signal from the fluorophore to be automatically separated from the background in an improved manner to produce an enhanced fluorescent signal. This enhancement of the fluorescent signal occurs by a particular instrument design, by the type of data collected and by a specific method used to process this data.

In co-pending application Ser. No. 751,746, a source such as a laser is pulsed to produce concentrated light energy at a particular frequency such as 780 nm. This light is directed to a specimen to obtain a fluorescence from particular fluorophore molecules in the specimen. This fluorescence continues for a period of time after the initiation of the fluorescence. A detector is provided to detect the fluorescence from the particular fluorophore molecules in the specimen. The detector is gaged to operate only for a particular period of time beginning after the initiation of the fluorescence of the particular fluorophore molecules in the specimen and ending before the completion of the fluorescence of the particular fluorophore molecules in the specimen. By gaging the detector in this manner, the signals produced from the fluorescence of the particular fluorophore molecules in the detector are enhanced relative to the signals representing background noise and the time dependence of these signals provides the information for a further discrimination between desired signal and background.

This invention provides an improvement in the system disclosed and claimed in co-pending application Ser. No. 751,746. In the system of this invention, the specimen is provided with characteristics to polarize the fluorescence produced in a specimen by pulses of light from a source such as a laser. The polarized components of the fluorescence in particular directions are detected to identify the specimen or, if the identity of the specimen is known, to identify the relative concentration of the specimen in a solution.

In one embodiment of the invention, light pulsed at a particular wavelength (e.g. 780 nm) fluoresces a specimen. The specimen may be combinations of an antigen (e.g., rubella) labelled with a fluorescent dye, unlabeled antigen or hapten and an antibody reactive with the antigen or hapten. The fluorescence polarized in a first direction (e.g. z-axis) parallel to the incident light modulations and in a second direction (e.g. x-axis) perpendicular to the first direction is measured.

A second specimen is then provided with the antigen and the antibody but without the dye. The same light as discussed above fluoresces the second specimen and polarizes the fluorescence. The fluorescence polarized in the first and second directions in the second specimen is measured. These measurements are processed in a microprocessor with the measurements in the z and x directions in the first specimen to identify the antigen or, when the antigen is known, to identify the concentration of the antigen in the first specimen.

When the light is pulsed, the measurements are made in a time window beginning after the initiation, and terminating before the end, of the fluorescence of the combination of the dye, the antibody and the antigen. Determinations as discussed above but without unlabeled antigen may be made of the antibody instead of the antigen.

Figure 1:
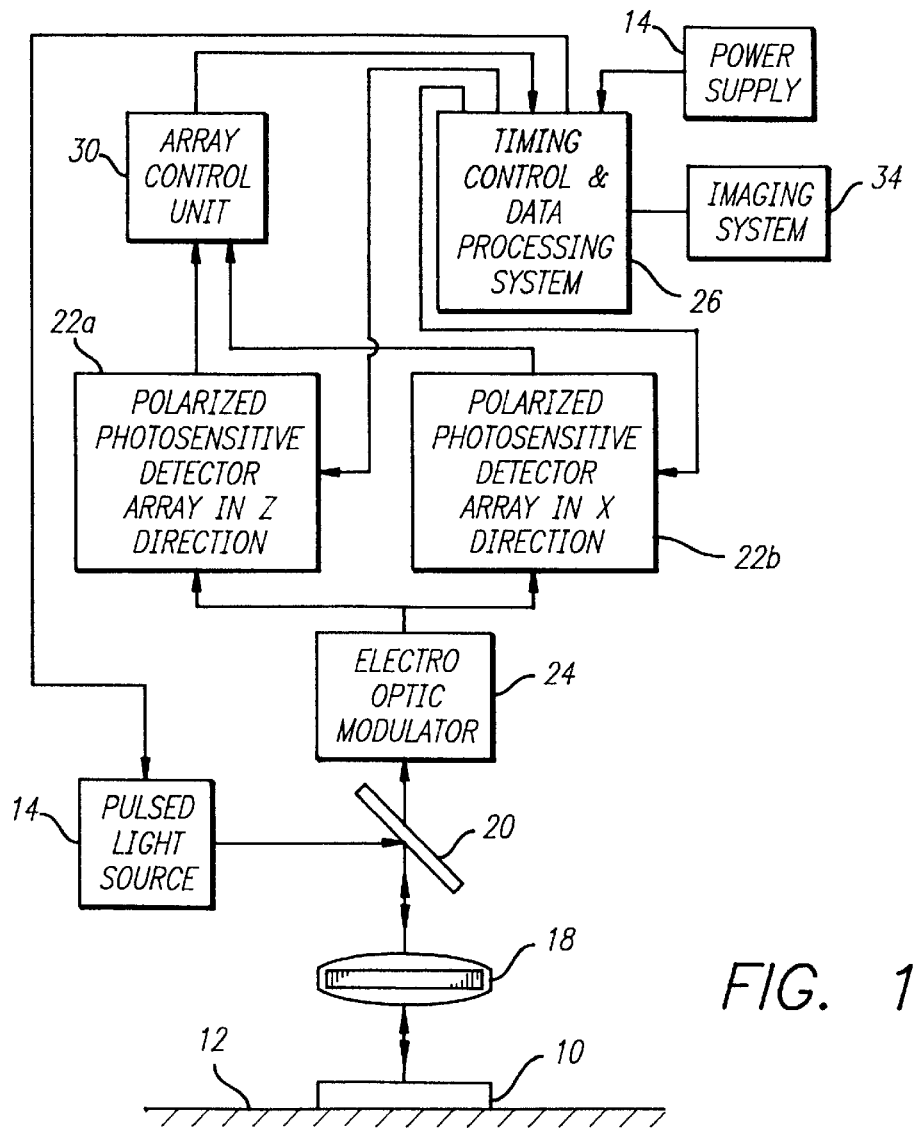
FIG. 1 is a schematic diagram, primarily in block form, of a system constituting one embodiment of this invention for identifying the fluorescence of a specimen by light directed on a pulsed basis to the specimen.
Figure 4:
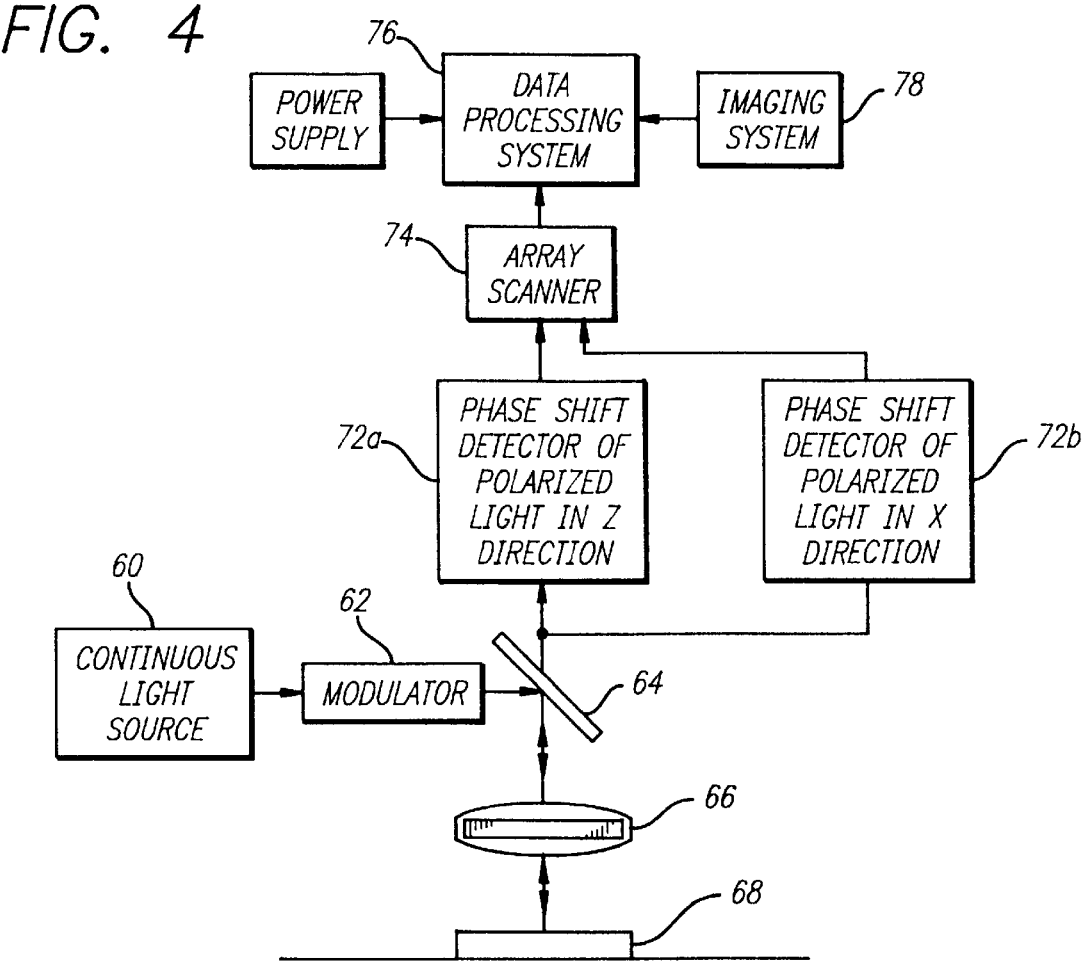
Figure 5:
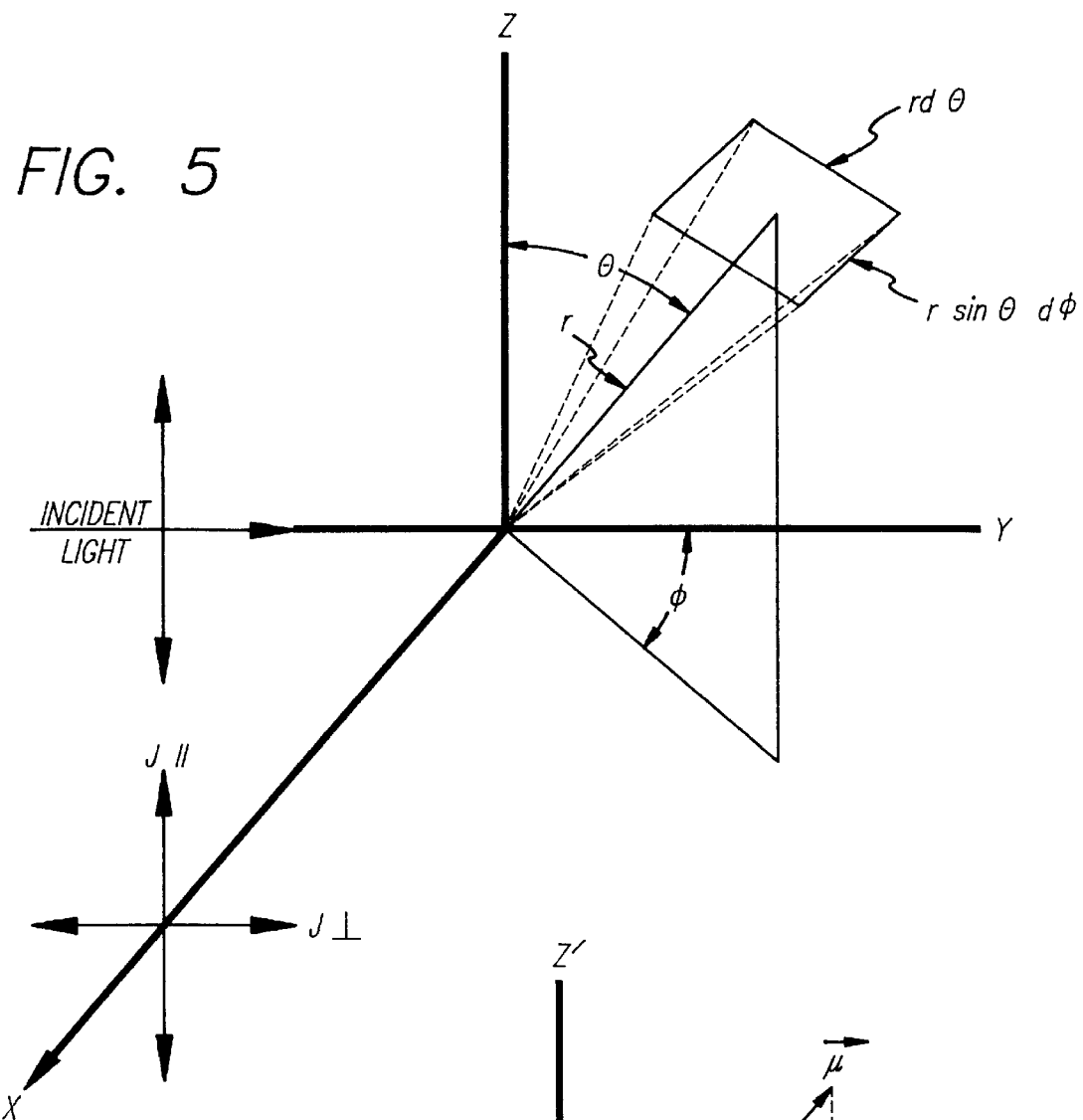
Figure 6:
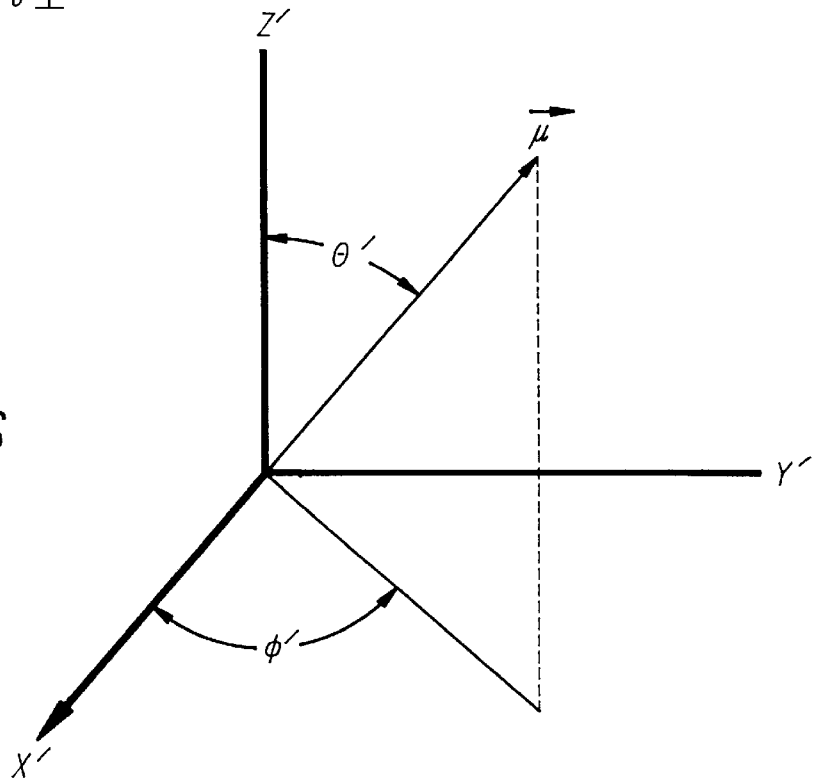

FIG. 4 is a schematic diagram, primarily in block form, of a system constituting a second embodiment of this invention for identifying the fluorescence of a specimen by modulated light directed on a continuous basis to the specimen; and FIG. 5 is a geometrical arrangement for the observation of polarized components provided by the system embodiments shown in FIGS. 1 and 4; and FIG. 6 is a coordinate system showing the orientation of an emission dipole with respect to geometric axes fixed in a rotating molecule.

The system of this invention constitutes an improvement of the system disclosed and claimed in application Ser. No. 751,746. The system disclosed and claimed in application Ser. No. 751,746 is accordingly incorporated by reference in this application to complete any deficiencies in the disclosure of this application or to implement the disclosure in this invention.

FIG. 1 illustrates a first embodiment of this invention. As shown in FIG. 1, a specimen 10 to be analyzed is positioned on a stationary surface 12. A light source 14 is controlled to direct a pulse or burst of concentrated light energy toward a dichroic mirror 20. Preferably the light source 14 constitutes a laser which produces collimated, substantially coherent and polarized light at a particular wavelength such as approximately 780 nm. Preferably the range of wavelengths from the laser is between about 625 nm and 850 nm. However, other types of light sources than lasers may also be used without departing from the scope of the invention.

The mirror 20 directs the light energy through an objective lens 18 to the specimen 10. The specimen 10 has properties of fluorescing when light at a particular wavelength such as approximately 780 nanometers is directed to the specimen. Light filters may be included in the excitation and emission beams, particularly when other light sources than lasers are used, to isolate the fluorescence emission and to limit excitation to a single or narrow band of wavelengths.

The specimen may include a material to be detected. For example, the material may constitute molecules of a disease in a patient's body. Molecules of the rubella disease are a good example of this. As another example, the material may constitute digoxin. Digoxin stimulates the heart muscle. The material may also constitute drugs for treating various diseases and vaccines for detecting various diseases and other chemicals that perform special functions such as the special functions provided by digoxin. The term "antigen" may be considered to be generic in the specification and the claims to these different materials.

The specimen 10 may also include a material which combines physically or chemically with the antigen. Such a material may be considered to be generically described in the specification and the claims by the term "antibody". The antibody may be a DNA fragment or a chemical. The specimen 10 may also include a dye combined chemically or physically with the antigen or antibody. Preferably the dye has properties of producing a polarization of the fluorescence produced in the specimen 10 or, if the light directed to the specimen 10 is already polarized, a redirection of the polarization.

Although the invention is disclosed as relating to the detection of the characteristics of the antigen, it will be appreciated that the invention may relate to the detection of the characteristics of the antibody.

Certain derivatives of phthalocyanine such as naphthalocyanine and of porphine such as monoaza, diaza, and triazaphorphine and dihydro and tetrahydro porphines, sapphyrins, corrins, pyrilliums and indanthrenes have been found to be satisfactory dyes. Porphines (now commonly designated as "porphyrine") have relatively long decay times (to about twenty nanoseconds (20 nsec.)) but absorb light energy usually at wavelengths below about seven hundred nanometers (700 nm). Reduction of one (1) double bond in the porphine ring to give a dihydroporphine decreases the decay time but at the same time moves the absorption upwardly in wavelengths toward the infrared region. Further reduction of double bonds in the porphine (now commonly designated as "porphyrine") ring produces further changes in the same direction.

In any particular assay, the best compromise of properties is often reached empirically. Modification of properties in both the phthalocyanine and the porphine (now commonly designated as "porphyrine") series can be further accomplished by complexation with light metal ions such as $Mg^{2+}$ or light atoms such as silicon readily forming octahedral complexes. Heavier elements such as Cr, Fe, Co, Ni, Cu and Ge form complexes useful for some applications. An additional goal accomplished by insertion of aluminum or preferably silicon is to reduce the quenching observed for phthalocyanines and certain porphines and reduced porphines when they are placed in protic solvents as compared to solvents such as dimethylsulfoxide (DMSO).

The insertion of heavy ions favors transition to the triplet state with loss of fluorescence but with the appearance of phosphoresence. In addition, the properties may be further modified by a variety of chemical groups added in the peripheral, meso or axial positions.

It has been found that the properties of dyes such as phthalocyanines and porphines in producing a polarization of the fluorescence in the specimen 10 are enhanced when the phthalocyanines or porphines become unbalanced in certain directions. This may be accomplished by adding chemical groups to these molecules in certain directions so as to alter the symmetry of the molecule.

In one embodiment of the invention, a first specimen is obtained by disposing the antigen, the antibody and the antigen labeled with the dye in an aqueous a solution. The labelling may be accomplished in a conventional manner. Over a period of time the molecules combine to produce a mixture of free and bound forms of the antigen, the labelled antigen and the antibody.

Antigen+Labelled Antigen+Antibody

Antigen+Labelled Antigen+Antibody+Antigen Antibody +Labelled Antigen Antibody

In a second embodiment, a first specimen is obtained by disposing, in an aqueous solution, the antibody and the antigen labelled with the dye.

Labelled Antigen+Antibody

Labelled Antigen Antibody+Labelled Antigen+Antibody

The light energy from the source 14 excites a fluorescence in the different elements in the specimen, thereby producing a polarization in the fluorescence from the specimen. This polarization is produced primarily as a result of the properties of the dye in the specimen 10. This polarized fluorescence passes through the objective lens 18 which forms an image of the polarized fluorescence. The light then passes through the half-silvered mirror 20 to polarized photosensitive detector arrays 22a and 22b.

At a time $t_A$, an electro optical modulator 24 opens a to allow the polarized fluorescence passing through the half-silvered mirror 20 to be introduced to the polarized photosensitive detector arrays 22a and 22b. The time $t_A$ is selected to occur after the light source 14 has produced the pulse of light and the different elements in the specimen have been fluoresced by such pulse of light. This time $t_A$ is determined by control circuitry included in a data processing module 26 which operates to provide timing controls.

At a time $t_B$, the data processing module 26 closes the electro optical modulator 24 to prevent the polarized fluorescence from passing to the polarized photosensitive detector arrays 22a and 22b. The time $t_B$ is selected to occur during the time that the fluorescence is still being produced by the combination of the dye, the antibody and the antigen. The time between $t_A$ and $t_B$ may be in the order of ten nanoseconds (10 nsec.) to fifteen nanoseconds (15 nsec.). By closing the electro optical modulator at the time $t_B$, the signals detected in the arrays 22a and 22b from the polarized components of fluorescence from the combination of the dye, the antibody and the antigen are enhanced relative to the signals detected from other polarized components of the fluorescence in the specimen 10 and the time dependence of these signals provides the information to produce a further enhancement in the signal-to-noise ratio.

Each of the detector arrays 22a and 22b may include detectors for sensing the amount of the polarized components in a particular direction. For example, the detector array 22a may detect the polarized components in the z direction passing to the detectors in the array. The z direction is the direction of the polarized component of the incident light modulations. Similarly, the detector array 22b may detect the polarized components in the x direction passing to the detectors in the array 22b. The x direction is perpendicular to the direction.

The polarized component detected by the detector array 22a in the z direction represents the polarized component of the fluorescence produced in the specimen 10 in the z direction from all of the elements, and different combinations of elements, in the specimen 10. This includes the dye, the antibody, the antigen, the combination of the dye and the antigen and the combination of the dye, the antibody and the antigen.

The polarized component of the fluorescence detected by the detector array 22b in the x direction represents the polarized component of the fluorescence produced in the specimen 10 in the x direction from all of the elements, and different combinations of elements, in the specimen 10. This includes the dye, the antibody, the antigen, the combination of the dye and the antibody or antigen and the combination of the dye, the antibody and the antigen and the combination of the antigen and the antibody.

The polarized component of the fluorescence passing to the detector array 22a differs from the polarized component of the fluorescence passing to the detector array 22b. This results in part from the effect of the dye in the specimen and from the polarized component of the fluorescence. It also results in part from the combination of the antibody and the antigen with the dye since this combination increases the molecular weight of the combination and thereby affects the angle through which the fluorescence is rotated as a result of the time delay and rotational motion.

Figure 2:
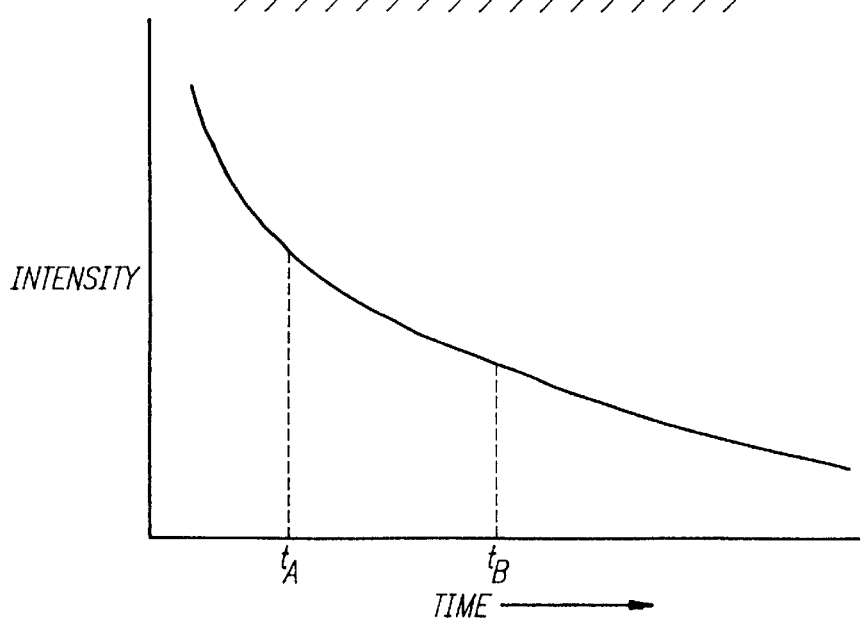
FIG. 2 is a graph illustrating the time that the pulsed fluorescence produced by the system shown in FIG. 1 is measured.

FIG. 2 schematically illustrates a curve showing time in the horizontal axis and, in the vertical axis, the intensity of the fluorescence produced in the specimen 10 as a result of a pulse of light from the light source 14. FIG. 2 also illustrates the relative times $t_A$ and $t_B$. As will be seen, the fluorescence in the specimen 10 actually commences before the time $t_A$ and continues after the time $t_B$. However, the intensity of the fluorescence between the time $t_A$ and the time $t_B$ is optimal from a measurement standpoint since the fluorescence of the dye is changing at a rate different from that of the background. As a result, measuring the fluorescence before the time $t_A$ and after the time $t_B$ results in the production of signals which accentuate noise and which cloud the signals produced in the time between $t_A$ and $t_B$ to represent the fluorescence in the combination of the dye, the antibody and the antigen.

Figure 3:
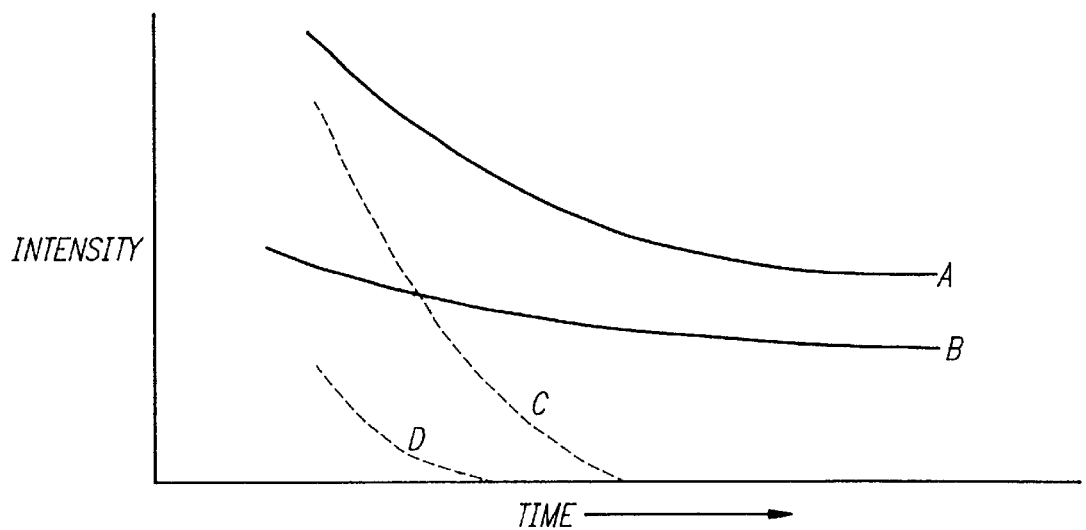
FIG. 3 illustrates curves of measurements by the system shown in FIG. 1 when the dye is present in the specimen and also when the dye is not present in the specimen.

FIG. 3 also schematically shows a curve in which time is plotted along the abscissa and intensity is plotted along the ordinate. However, the intensity in FIG. 3 represents the intensity of the polarized component of the fluorescence. A curve A in FIG. 3 indicates the intensity of the component of the fluorescence detected by the detector array 22a polarized in the z direction. Similarly, a curve B in FIG. 3 indicates the intensity of the component of the fluorescence detected by the detector array 22b polarized in 4 the x direction.

T he detectors i n each of the arrays 22a and 22b produce signals representing the polarized component of the fluorescence produced at an individual position in the specimen 10. The signals from the detectors in each of the arrays 22a and 22b are introduced to an array control unit 30. The array control unit 30 operates to pass the signals sequentially from the successive detectors in the arrays 22a and 22b to the data processing unit. In this way, the data processing unit 26 sequentially produces signals representing the polarized light at different positions in the specimen 10. The signals produced by the d at a processing unit 26 may be introduced to an imaging system 34 to provide a visual display of the image represented by such signals.

It will be appreciated that other apparatus may be used to sequentially detect the polarized component of the fluorescence from successive positions in the specimen 10. For example, light from the source 14 may be directed to a rotatable mirror which then directs the light to successive positions in a particular direction in the specimen 10. Similarly, two (2) mirrors may be rotated, each in a coordinate direction relative to the other, to scan the fluorescence in the specimen 10 in a pair of coordinate directions such as the x and y directions. Alternatively, the specimen 10 may be moved relative to the detector arrays 22a and 22b to obtain an indication of the fluorescence at different positions in the specimen 10. Various embodiments for fluorescing the specimen and for detecting the fluorescence are disclosed in co-pending application Ser. No. 751,746 and are considered to be a part of this disclosure.

A second specimen is then provided which is the same as the specimen 10 except that the dye is not included. Measurements are then made in a manner similar to that described above to determine the polarity of the fluorescence in the z direction and the polarity of the fluorescence in the x direction. The components of the light polarized in the z and x directions are respectively indicated at C and D in FIG. 3.

The data processing system 26 then processes the measurements of the polarization of the specimen 10 in the z and x directions and the polarizations of the fluorescence of the second specimen in the z and x directions. In effect, the data processing system subtracts the signals in the second specimen from the signals from the first specimen for each of the z and x directions. The data processing system then processes the resultant signals to provide a resultant measurement. The resultant measurement indicates the combination of the dye, the antibody and the antigen. It provides an indication of the existence of a particular antigen in the specimen if the antigen is not known or the existence of a particular antibody in the specimen if the antibody is not known. This results from the combination of the particular antigen with the antigen. If the antigen is already known, it provides an indication of the concentration of the antigen or the antibody in the specimen. It will also be appreciated that other apparatus may be used to detect the polarized components from a single position in the specimen 10 either at successive times or at a single time. It will also be appreciated that other apparatus may be used to detect the total intensity of the fluorescence without regard to polarization.

FIG. 4 illustrates another embodiment of the invention. In this embodiment, light from a source 60 is provided on a continuous basis. Except that it is continuous instead of pulsed, the light from the source 60 is the same as the light from the source 14 in FIG. 1. The light from the source 14 is modulated as at 62. These modulations may be amplitude modulations.

The light from the modulator 62 then passes to a half silvered mirror 64 corresponding to the mirror 20 in FIG. 1. The light reflected by the mirror 64 passes through a lens 66 corresponding to the lens 18 in FIG. 1. The light then passes to a specimen 68 corresponding to the specimen 10 in FIG. 1. The specimen may include a dye, an antibody and an antigen in a manner similar to that described above. The light produces a fluorescence in the specimen, thereby resulting in the production of the polarized components in the fluorescence.

The polarized components of the fluorescence from the specimen 68 passes through the mirror 64 to phase shift detectors 72a and 72b. The phase detector 72a detects the phase shifts produced in the polarized components in the z direction and capable of being detected as a result of the amplitude modulations produced by the modulator 62 on the light from the source 60. The phase detector 72b detects the phase shifts produced in the polarized components in the x direction and capable of being detected as a result of the amplitude modulations by the modulator 62 on the light from the source 60. As in the embodiment shown in FIG. 1, the z direction is in the direction of polarization of the incident light modulations and the x direction is perpendicular to the z direction.

An array scanner 74 scans the indications from the phase shift detector 72a to determine the phase shift of the polarized components of the fluorescence in the z direction at progressive positions in the specimen 68. The array scanner 74 also scans the indications from the phase shift detector 74b to determine the phase shift of the polarized components of the fluorescence in the x direction at progressive positions in the specimen 68. The signals produced by the array scanner 74 are introduced to a data processing system 76 for processing.

A second specimen is then scanned in a manner similar to that described above. The second specimen is identical to the first specimen except that it does not include a dye. The resultant signals produced in the array scanner 74 to represent the polarized components of the fluorescence in the z and x directions are also introduced to the data processing system 76. The data processing system 76 processes the signals produced from the second specimen to represent the polarized components of the fluorescence in the z and x directions. The data processing system then processes the signals from the first and second specimens to obtain an output indication. The output indication produced by the data processing system 76 provides an identification of the antigen or antibody or, if the antigen or antibody is known, an identification of the concentration of the antigen or the antibody. The signals produced by the data processing system 76 may be introduced to an imaging system 78 to provide an identification of the specimen 68 at different positions on the specimen.

The apparatus described above has certain important advantages. The rates of rotary brownian motion of a luminant species are determined by analyzing the transient state intensities polarized parallel to, and perpendicular to, the direction of the polarized components of the excitation. By determining such rates of rotary brownian movement of the luminescent species, information for the performance of homogeneous binding assays can be obtained.

Suitable analysis of the transient state intensities of the polarized components of the fluorescence parallel to, and perpendicular to, the direction of the excitation modulations can separate the effects due to luminescence decay from those due to rotation. The effects due to rotation immediately afford the information for the performance of homogeneous binding assays, i.e. binding assays based upon a simple mix, incubate and read procedure with no separation steps for assessing the bound and free concentrations of the luminescent probe being used for the specific assay in question.

The following mathematical analysis has been prepared by applicants to indicate the operation of the system of this invention. This analysis provides a mathematical support for the operation of the system constituting this invention.

INTRODUCTION

Fluorescence assays are widely applied in chemistry, biochemistry and immunology. Usually these assays involve the detection of an added fluorescence tracer or sometimes the detection of a fluorescence species arising as a result of a chemical reaction. All such assays are limited in sensitivity not because there is an insufficient number of photons emitted from the sample, but because of the almost universal adventitious background which obscures the signal of interest. The problem of segregating out the signal from the combined signal and background fluorescence is dealt with conventionally by discrimination on the basis of wavelengths of excitation and emission. This methodology has been pushed to the practical limit by monochromators and interference filters or combinations of these.

An entirely different means of discrimination between signal and "noise" rests upon an analysis of the time dependence of the fluorescence intensity observed after a flash excitation. In a previous application we delineated a variety of new fluorescence measuring instruments based upon such an analysis. In this application we show how such instruments can give a dramatic increase in the sensitivity of all types of fluorescence measurements provided that the proper data are collected and subsequently utilized.

THEORY

If only the total fluorescence emission is observed the time dependence allows discrimination on the basis of the decay times of the various fluorescent species present. If, instead, the two polarized components in the emission are followed, additional discrimination on the basis of rotary brownian motion is possible. The fact that such detailed information is contained in the time dependent fluorescence has been long known, but until now satisfactory methods for extracting this information have been lacking.

In the absence of perturbing factors the rate of emission of energy from an assembly of excited molecules decreases exponentially with time. Information about the nature and orientation of the emitters and the rate of emission of energy can be found by sampling the radiation intensity from within an integrating sphere surrounding the fluorescent sample.

Usually measurements with an integrating sphere are not convenient and instead the rate of emission per unit solid angle (an intensity) at some particular angle is used as an index of the total rate of emission. Moreover, the dependence of intensity upon the direction of observation and more particularly the dependence of the intensities of the polarized components upon time are the crucial factors in our analysis. However, it is necessary to relate these quantities to the total rate of emission of energy as would be observed with an integrating sphere. The geometrical arrangement for the necessary intensity measurements is shown in FIG. 5. Any one of a number of other arrangements would give equivalent results, cf., for example, Weber, G., J. Opt. Soc. America, 46, 962 (1956) Monnerie, L. and Neel, J. Journal de Chimie Physique, 62, 504 (1965); Deranleau, D., Anal. Biochem., 16, 438 (1966); Edwards, L. O. and Simpson, W. T., J. Chem. Phys., X, 4237 (1970); Claesson, S. and Odani, H., Discuss. Faraday Soc., No. 49, 268 (1970); Lavorel, J. et al., Biochimie, X, 161 (1972); Wampler, J. and de Sa, R., Anal. chem., 46, 563 (1974).

The polarized components, $J_{II}$ and $J_\perp$ are the rates of emission of energy (in arbitrary instrument units) per unit solid angle, i.e., intensity as observed in the x direction. To determine the relationship between $J_{II}$ and $J_\perp$ and the total rate of emission of energy in the same instrument units we integrate over a spherical sskin surrounding the sample. For simplicity, the sample is assumed to consist of randomly oriented, stationary dipoles excited by light linearly polarized in the z direction. If the molecules are not stationary then the following calculation corresponds to an instantaneous comparison between the initial total rate of emission of energy, E(O), and the initial "intensities" $J_{II}(0)$ and $J_\perp(0)$ after a short excitation flash. The sample contained within the spherical volume of radius, r, contains v uniformly distributed luminescent centers per unit volume. The number within the pyramidal volume element is:

$$dN = \frac{vr^3}{3} \sin\theta d\theta d\phi \quad (1)$$

These centers or molecules have different probabilities of being excited (optical selection) by the incident light depending upon the angle $\theta$ between the exciting field and any particular absorption dipole, those dipoles being parallel to the z axis having the greatest probability of absorbing. The probability is proportional to the square of the magnitude of the component of the incident field in the direction of the dipole. Hence, the total number, $N_T$, excited within the spherical sample is:

$$N_T = \int_0^{2\pi} \int_o^\pi \frac{vr^3}{3} \sin\theta \cos^2\theta d\theta d\phi \quad (2)$$

The total rate of emission of energy is proportional to $N_T$, $E=\delta N_T$. When the molecules within the volume element emit, the contribution to $J_{II}$ is $$\frac{\kappa v r^3}{3} \sin\theta \cos^4\theta d\theta d\phi \quad (3)$$

Note that the second factor of $\cos^2\theta$ arises from the projection of r on the z axis which projection gives the electric field of the emitting dipole, (i.e., the direction in which $J_{II}$ is polarized), in the z direction, and when squared gives a quantity proportional to the rate of emission of energy in directions perpendicular to the z axis. Similarly, the contribution to $J_\perp$ is:

$$\frac{\kappa v r^3}{3} \sin^3\theta \cos^2\theta \cos^2\phi d\theta d\phi \quad (4)$$

The integrated expressions are:

$$E = \frac{\kappa v r^3}{3} \int_0^{2\pi} \int_0^\pi \cos^2\theta \sin\theta d\theta d\phi = \frac{4\pi\kappa v r^3}{9} \quad (5)$$

$$J_{\|} = \frac{\kappa v r^3}{3} \int_0^{2\pi} \int_0^\pi \cos^4\theta \sin\theta d\theta d\phi = \frac{4\pi\kappa v r^3}{15} \quad (6)$$

$$J_\perp = \frac{\kappa v r^3}{3} \int_0^{2\pi} \int_0^\pi \sin^3\theta \cos^2\theta \cos^2\phi d\theta d\phi = \frac{4\pi\kappa v r^3}{45} \quad (7)$$

Hence, $$E = J_{\|} + 2J_\perp \quad (8)$$

and $$\frac{J_{\|} - J_\perp}{J_{\|} + J_\perp} = 1/2 \quad (9)$$

Thus it is seen that the quantity $J_{II}+2J_\perp$ may be expected to decay exponentially with time since this is the particular combination of $J_{II}$ and $J_\perp$ that is equal to the total rate of the emission of energy from an assembly of excited luminescent molecules.

Molecules in fluid solutions at ordinary temperatures are in a state of violent, random translational and rotational motion (brownian motion). Because of this rotational motion the direction of the electric field in the emission from any individual molecule will be different from that of the original excited dipole even if the excitation and emission moments are parallel. The effect on $J_{II}$ and $J_\perp$, observed as functions of time, t, is to make $J_{II}$ decrease more rapidly and $J_\perp$ to decrease less rapidly with time than does E. The rate of rotational brownian motion of the molecule or more pertinently of the emission dipole is a function of the size, shape, topography and flexibility of the molecule and of the properties of the solvent. Hence, it is obvious that a great deal of detailed information is contained in the functions $J_\parallel(t)$ and $J_\perp(t)$.

The problem of extracting this information has been considered by a number of workers. Jablonski (Jablonski, A. Bull. de L'Academie Polonaise des Sciences. Serie Sci. math. astr. phys., 8, 259–264 (1960) introduced the idea of emission anisotropy, a function independent of the rate of decay of the excited state by virtue of being normalized by E(t). Wahl (Wahl, P. Compt. Rend. Acad. Sci., Paris, 260, 6891 (1965). made an analysis of $J_\parallel(t)$ and $J_\perp(t)$ in terms of decay times and molecular geometry. Yguerabide and co-workers, Yguerabide, J., Epstein, H. F. and Stryer, L. J. Mol. Biol. 51, 573–590 (1970) used earlier results to make an analysis in terms of rapid reactions and molecular motions or rearrangements.

By far, the most comprehensive and penetrating analysis of transient-state or time-dependent fluorescence has been made by Tao (Biopolymers, 8. 609–632 (1969)). Tao gives the time dependent intensity functions, $I_\parallel(t)$ and $I_\perp(t)$ normalized so that at zero time, $I_\parallel(0)+2I_\perp(0)=1$. Note that for a single species $I_\parallel(t)$ and $I_\perp(t)$ are proportional to $J_\parallel(t)$ and $J_\perp(t)$ respectively.

The general forms of $I_\parallel$ and $I_\perp$ for a particle of arbitrary shape and hydrodynamic properties and for any orientation of the absorption and emission dipoles are:

$$I_\parallel(t) = P_2\cos\lambda \left[ \frac{1}{3} + \frac{4}{15} C(t) \right] P(t) + \frac{\sin^2\lambda}{2} P(t) \quad (10)$$

$$I_\perp(t) = P_2\cos\lambda \left[ \frac{1}{3} - \frac{2}{15} C(t) \right] P(t) + \frac{\sin^2\lambda}{2} P(t) \quad (11)$$

In these equations $P_2 \cos\lambda$ is the Legendre polynomial of order 2 and is equal to $\frac{1}{2}(3\cos^2\lambda - 1)$ where $\lambda$ is the angle between the absorption and emission moments as constrained by the molecular architecture. P(t) is the "probability that the fluorescent state will remain excited at time t". The function C (t) [identical with Tao's $C_{20}(t)$] depends upon the geometry of the molecule or more specifically upon the rotary brownian motion of the molecule and upon the orientation of the emission dipole with respect to the geometric axes of the molecule.

For a molecule of arbitrary size and shape with no assumed symmetry, $$C(t) = \frac{3\mu_\alpha^2\mu_\beta^2}{\mu^4} e^{-3(D_\gamma+D)t} + \frac{3\mu_\alpha^2\mu_\gamma^2}{\mu^4} e^{-3(D_\beta+D)t} + \frac{3\mu_\beta^2\mu_\gamma^2}{\mu^4} e^{-3(D_\alpha+D)t} + \frac{3}{4}(B+A)e^{-(6D-2\Delta)t} + \frac{3}{4}(B-A)e^{-(6D+2\Delta)t} \quad (12)$$

In equation (12), $D = \frac{1}{3}(D_\alpha + D_\beta + D_\gamma)$ where $D_\alpha$, $D_\beta$ and $D_\gamma$ are the rotary brownian diffusion coefficients for rotation of the molecule about the x, y, and z axes, respectively (cf. FIG. 6).

$$\Delta = [D_\alpha^2 + D_\beta^2 + D_\gamma^2 - D_\alpha D_\beta - D_\alpha D_\gamma - D_\beta D_\gamma]^{1/2} \quad (13)$$

$$A = \frac{D_\alpha}{\Delta}\left(\frac{\mu_\alpha^4 + 2\mu_\beta^2\mu_\gamma^2}{\mu^4}\right) + \frac{D_\beta}{\Delta}\left(\frac{\mu_\beta^4 + 2\mu_\alpha^2\mu_\gamma^2}{\mu^4}\right) + \quad (14)$$

-continued
$$\frac{D_\gamma}{\Delta}\left(\frac{\mu_\gamma^4 + 2\mu_\alpha^2\mu_\beta^2}{\mu^4}\right) - \frac{D}{\Delta}$$

$$B = \left[\frac{\mu_\alpha^4 + \mu_\beta^4 + \mu_\gamma^4}{\mu^4}\right] - \frac{1}{3} \quad (15)$$

The meaning of the $\mu$'s is shown in FIG. 6 and equations (16), (17) and (18).

$$\mu_\alpha = \mu \sin\theta' \cos\theta' \quad (16)$$

$$\mu_\beta = \mu \sin\theta' \sin\theta' \quad (17)$$

$$\mu_\gamma = \mu \cos\theta' \quad (18)$$

The coefficients in Equation (12) can now be expressed in terms of $\theta'$ and $\phi'$ instead of the $\mu$'s, $$\frac{\mu_\alpha^2\mu_\beta^2}{\mu^4} = \sin^4\theta'\cos^2\phi'\sin^2\phi' \quad (19)$$

$$\frac{\mu_\alpha^2\mu_\gamma^2}{\mu^4} = \sin^2\theta'\cos^2\theta'\cos^2\phi' \quad (20)$$

$$\frac{\mu_\beta^2\mu_\gamma^2}{\mu^4} = \sin^2\theta'\cos^2\theta'\sin^2\phi' \quad (21)$$

The range of the right hand side of the Equations (19), (20) and (21) is in each case from 0 to $\frac{1}{4}$.

The expressions needed for A and B can be expressed similarly.

$$\frac{\mu_\alpha^4 + 2\mu_\beta^2\mu_\gamma^2}{\mu^4} = \sin^2\theta'[\sin^2\theta'\cos^4\phi' + 2\cos^2\theta'\sin^2\phi'] \quad (22)$$

$$\frac{\mu_\beta^4 + 2\mu_\alpha^2\mu_\gamma^2}{\mu^4} = \sin^4\theta'\sin^4\phi' + 2\sin^2\theta'\cos^2\theta'\cos^2\phi' \quad (23)$$

$$\frac{\mu_\gamma^4 + 2\mu_\alpha^2\mu_\beta^2}{\mu^4} = \cos^4\theta' + 2\sin^4\theta'\sin^2\phi'\cos^2\phi' \quad (24)$$

The range of the right hand side of Equations (22), (23) and (24) is 0 to 1. In Equation (24) the maximum is at $\theta'=0$ for any $\phi'$.

For B the expression becomes $$B = [\sin^4\theta'\cos^4\phi' + \sin^4\theta'\sin^4\phi' + \cos^4\theta'] - \frac{1}{3} \quad (25)$$

The range of B is from 0 to $\frac{2}{3}$ with maxima at $\theta'=0$ and at $\theta'=\phi'=90°$.

Equation (12) can now be used readily to compute C(t) from assumed values of $\theta'$, $\phi'$, $D_\alpha$, $D_\beta$, and $D_\gamma$.

In the expression for $\Delta$, equation (13), if $D_\alpha=D_\beta=D_\gamma$ (sphere) the quantity $\Delta$ goes to zero. This results in division by zero in equation (14). Equation (13) can be rewritten as:

$$2\Delta^2 = (D_\alpha - D_\beta)^2 + (D_\beta - D_\gamma)^2 + (D_\gamma - D_\alpha)^2 \quad (26)$$

Rewriting equation (15) as $$3\mu^4 B = (\mu_\alpha^2 - \mu_\beta^2)^2 + (\mu_\beta^2 - \mu_\gamma^2)^2 + (\mu_\gamma^2 - \mu_\alpha^2)^2 \quad (27)$$

and rewriting equation (14) as:

$$3\Delta\mu^4 A = (\mu_\alpha^2 - \mu_\beta^2)^2(D_\alpha - D_\gamma + D_\beta - D_\gamma) + (\mu_\beta^2 - \mu_\gamma^2)^2$$

$$(D_\beta - D_\alpha + D_\gamma - D_\alpha) + (\mu_\gamma^2 - \mu_\alpha^2)^2(D_\gamma - D_\beta + D_\alpha - D_\beta)$$

In equations (26, 27, and 28) the expression of A, B and $\Delta$ in terms of differences between $D_\alpha$, $D_\beta$ and $D_\gamma$ on one hand and between $\mu_\alpha^2$, $\mu_\beta^2$, and $\mu_\gamma^2$ on the other suggests the following transformation:

$$x_\alpha = (\mu_{\beta 2}^2 - \mu_\gamma^2)^2; \; x_\beta = (\mu_\gamma^2 - \mu_\alpha^2)^2; \; X_\gamma = (\mu_\alpha^2 - \mu_\beta^2)^2 \qquad (29)$$

$$y_\alpha = (D_\beta - D_\gamma); \; y_\beta = (D_\gamma - D_\alpha); \; y_\gamma = (D_\alpha - D_\beta) \qquad (30)$$

With these transformations:

$$2\Delta^2 = y_\alpha^2 + y_\beta^2 + y_\gamma^2 \qquad (31)$$

$$3\mu^4 B = x_\alpha + x_\beta x_\gamma \qquad (32)$$

$$3\Delta\mu^4 A = x_\alpha(y_\beta - y_\gamma) + x_\beta(y_\gamma - y_\alpha) + x_\gamma(y_\alpha - y_\beta). \qquad (33)$$

Equations (29) and (30) define the vectors $\vec{x}$ and $\vec{y}$;

$$\vec{x} = (x_\alpha, x_\beta, x_\gamma) \qquad (34)$$

$$\vec{y} = (y_\alpha, y_\beta, y_\gamma) \qquad (35)$$

Denoting the length of the vector $\vec{y}$ by $|\vec{y}|$ gives:

$$2\Delta^2 = |\vec{y}|^2 \text{ or } \Delta = \frac{|\vec{y}|}{\sqrt{2}} \qquad (36)$$

$$3\mu^4 B = x_\alpha + x_\beta + x_\gamma \qquad (37)$$

Introducing the vector $\vec{z} = (z\alpha, z\beta, z\gamma) = \sqrt{2} \; \vec{x} \times \vec{y}$ gives:

$$3\mu^4 A = z_\alpha + z\beta + z\beta \qquad (38)$$

where X denotes the cross product.

Now define new vectors $\vec{U}$ and $\vec{V}$ by $$U_\alpha = \frac{x_\alpha}{\mu^4}; \; U_\beta = \frac{x_\beta}{\mu^4} \; U_\gamma = \frac{x_\gamma}{\mu^4} \qquad (39)$$

$$V_\alpha = \frac{y_\alpha}{|\vec{y}|}; \; V_\beta = \frac{y_\beta}{|\vec{y}|}; \; V_\gamma = \frac{y_\gamma}{|\vec{y}|} \text{ with} \qquad (40)$$

$$\vec{U} = (u_\alpha, u_\beta, u_\gamma); \; \vec{V} = (v_\alpha, v_\beta, v_\gamma) \qquad (41)$$

Equation (40) indicates $\vec{V}$ to be a unit vector, i.e. $|\vec{V}|=1$, from equations (36–41);

We need to introduce the vector $\vec{W} = (W_\alpha, W_\beta, W_\gamma) = \vec{U} \times \vec{V}$ then $$3B = U_\alpha + U_\beta + U_\gamma \qquad (42)$$

$$3A = \sqrt{2} \; (w_\alpha + w_\beta + w_\gamma) \qquad (43)$$

Therefore, A does not depend upon the length of the vector $\vec{y}$ but upon only the angle between $\vec{x}$ and $\vec{y}$.

It may now be seen from equations (27 and 28) that when $D_\alpha = D_\beta = D_\gamma$, both A and B are zero since $\mu_\alpha = \mu_\beta = \mu_\gamma$.

For ellipsoids of revolution with $D_\alpha = D_\gamma$ and therefore $\mu_\alpha = \mu_\beta$ equations (31) become $$y_\gamma = 0; \; y_\alpha = -y_\beta \qquad (44)$$

$$x_\gamma = 0; \; x_\alpha = x_\beta \qquad (45)$$

and $2\Delta^2 = 2y_\alpha^2$ or $\Delta = y\alpha$ (46)

$$3\mu^4 B = 2x_\alpha \qquad (47)$$

or $$3\mu^4 A = -2x_\alpha \frac{y_\alpha}{|\vec{y}|} \qquad (48)$$

Therefore, A=B if $y_\alpha < 0$ or $D_\gamma > D_\beta$ A=−B if $y_\alpha > 0$ or $D_\gamma < D_\beta$ which confirms Tao's result (Tao's equation 49) for a body with an axis of symmetry.

The results above show that when $D_\alpha = D_\beta = D_\gamma$, although $\Delta = 0$ and therefore Tao's equation (46) for A leads to a division by zero, our equivalent equations (36, 37 and 38 or 42 and 43) do not involve the length of the vector $\vec{y}$ but only the angle of this vector with a fixed direction related to vector $\vec{x}$. According to this angle, when $D_\alpha$, $D_\beta$ and $D_\gamma$ tend to be equal $$B \to 0$$

and A varies between +B and −B as this angle varies.

In making computations the above results indicate that when $\mu_\alpha$, $\mu_\beta$ and $\mu_\gamma$ tend to be equal, both A and B should be set equal to zero, if the differences between $\mu_\alpha$, $\mu_\beta$ and $\mu_\gamma$ are less than the computer precision.

The analytical reason for this is that the vector $\vec{V}$ remains equal to 1 while the vector $\vec{U}$ decreases to zero when $\mu_\alpha, \mu_\beta$ and $\mu_\gamma$ become equal.

Now, in turn, $I_{||}(t)$ and $I_\perp(t)$ can be calculated for any assumed model by assigning a value for $\lambda$, the angle between the excitation and emission dipoles and for P(t).

Assuming a single decay constant for any one type of molecule, $$P(t) = e^{-kt} \qquad (49)$$

where k is the first order constant for decay of the fluorescent state.

As pointed out above $I_{||}$ and $I_\perp$ are proportional to $J_{||}(t)$ and $J_\perp(t)$, respectively. In order to use Tao's results they must be related to the experimentally accessible quantities, $J_{||}(t)$ and $J_\perp(t)$.

As shown in Equation (8).

$$E(t) = J_{||}(t) + 2J_\perp(t) \qquad (50)$$

For first order decay:

$$E(t) = E(O)e^{-kt} \qquad (51)$$

It must be appreciated that Tao's equations pertain to a single fluorescent species, i, for which he has normalized the intensity functions so that $$I_{i||}(0) + 2I_{i\perp}(0) = 1. \qquad (52)$$

Therefore, $$I_{i||}(0) + 2I_{i\perp}(0) = \frac{J_{i||}(0) + 2J_{i\perp}(0)}{E_i(0)} \qquad (53)$$

But for each species, we can express $E_i(O)$ in terms of a constant $q_i$, the "molar fluorescence" and the molar concentration, $M_i$.

$$E_i(0) = M_i q_i \qquad (54)$$

Since $J_{||}$ and $J_\perp$ bear a constant ratio to $I_{||}$ and $I_\perp$ respectively, at all t, we find that $$J_{i||} = M_i q_i I_{i||} \qquad (55)$$

$$J_{i\perp} = M_i q_i I_{i\perp} \qquad (56)$$

Equations (55) and (56) enable us to relate Tao's theory to the observable fluorescence of a single fluorescent species.

If instead of equation (49), P(t) is defined by $$P'(t) = \sigma e^{-kt} \tag{57}$$

then since P(t) is a probability $$\int_0^\infty P'(t)dt = 1 = \sigma \int_0^\infty e^{-kt}dt = \sigma \left[ \frac{e^{-kt}}{-k} \right]_0^\infty = \frac{\sigma}{k} \tag{58}$$

and $\sigma = k$

Hence $P'(t) = k\, e^{-kt}$ and $$I'^{iII}(0) + 2I'_{iI}(0) = \sigma \tag{59}$$

In these equations the primes are used only to indicate the different definition of P used in equation (57).

From equation (53):

$$\frac{I'_{i\|}(0) + 2I'_{i\perp}(0)}{\sigma} = \frac{J_{i\|}(0) + 2J_{i\perp}(0)}{E_i(0)} \tag{60}$$

since from equation (54)

$$E_i(0) = M_i q_i$$

$$I'_{i\|}(0) + 2I'_{i\perp}(0) = \frac{J_{i\|}(0) + 2J_{i\perp}(0)}{M_i q_i \left(\frac{1}{\sigma}\right)} \tag{61}$$

Hence, the effects of the choice of definition made in equation (57) as contrasted to that of equation (49) is absorbed in the experimentally determined value for $q_i$ and has no effect on the subsequent equations.

In actual experiments where more than one fluorescent species is present the J's must be represented by a summation which assumes that all of the individual fluorescence intensities are additive:

$$J_{II}(t) = \Sigma M_i q_i I_{i,II}(t) \tag{62}$$

$$J_\perp(t) = \Sigma M_i q_i I_{i,\perp}(t) \tag{63}$$

In the context of Equations (62) and (63) a fluorescent species is any one which is distinguishable on the basis of fluorescence properties from other material present in the sample, for example, free and bound forms of a fluorescent labeled ligand. Such a ligand bound to different types of sites and the various components giving rise to background fluorescence can each be treated as a separate species if it is somehow distinguishable in fluorescence properties.

These considerations lead to a crucial idea in segregating the fluorescence signals from each other, particularly in segregating the signals of "bound", "free" and the background.

This concept analogous to "excess fluorescence" involves the determination of the time dependent functions $I_{i,II}$ and $I_{i,\perp}$ for each species (or group of species) by measurements made under conditions such that essentially all of the observed signal is due to one species (or group of species) alone. Thus, if a fluorescent labeled ligand binds to some receptor of interest and the degree of binding is to be measured, the functions $I_{II}$ and $I_\perp$ must be determined for the "free" form (no receptor present), for the essentially completely bound form (extrapolation to infinite receptor concentration) and for the group of species in the blank.

To discriminate optimally between "bound" and "free" and the background places restrictions on the properties of the fluorescent label. First, and most obvious is that the wavelengths of excitation and emission of the label should be as distinct from that of the background as available instrumentation will tolerate without excessive sacrifices in sensitivity. This technology is well known and forms the foundation of current state-of-the-art fluorescence measurements.

In the present context the other restriction on the label has to do with decay time. In words, the decay time must be the best compromise to distinguish on the combined basis of rotational motion, molar fluorescence, and decay time between bound, free and background. These combined restrictions also dictate the optimal time window over which measurements must be taken. It should be noted that this window will not in general coincide with simply waiting until the background has totally disappeared because to do so would result in loss of the crucial information on molecular rotation. Attention must also be given to the relationship between decay time and the magnitudes of $J_{II}$ and $J_\perp$ at time zero. In the simplest case consider two fluorescent dyes of the same quantum yield and concentration but differing in decay time. According to Lord and Rees (Lord, Mary P. and Rees, A. L. G., Proc. Phys. Soc. (London), 58, p. 281 (1946), the steady state concentration of excited molecules is the same for two such dyes and the value of $J_{II}(O)+2J_\perp(O)$ will be expected to be inversely proportional to the decay time. The methodology for making the optimal choice of decay time by means of numerical simulations is delineated below.

The simulations are made possible by combinations of Equations (62) and (63) with Equations (10), (11), (49) and (51). These combinations allow any assumed values of the parameters $\lambda$, $D_\alpha$, $D_\beta$, $D_\gamma$, k, $\theta'$ and $\phi'$ to be used and permit calculation of a number of derived quantities, especially the concentration of "bound" or "free" ligand. Computation of these same quantities from experimental measurements utilizes a similar computational framework shown below. These concepts form the basis for assays based upon transient state fluorescence.

ADAPTATION & APPLICATION OF THEORY TO PRACTICAL MEASUREMENTS

In order to delineate, for illustration, the use of the equations given above it is expeditious to apply them to a simplified prototype assay in which the concentration of bound or free ligand is to be determined in a system containing only one type of bound and of free ligand and the fluorescent components in the blank.

For this system Equations (62) and (63) can be written as follows:

$$J_\|(t) = M_1 q_1 I_{1\|}(t) + M_2 q_2 I_{2\|}(t) + \sum_j M_j q_j I_{j\|}(t) \tag{64}$$

$$J_\perp(t) = M_1 q_1 I_{1\perp}(t) + M_2 q_2 I_{2\perp}(t) + \sum_j M_j q_j I_{j\perp}(t) \tag{65}$$

In Equations (64) and (65), the subscript "1" indicates "bound" and "2" indicates "free" ligand. The unknown components in the blank are denoted by the index "j".

The time dependent functions $I_{1II}$, $I_{1\perp}$, $I_{2II}$ and $I_{2\perp}$ can be evaluated empirically from measurements of $J_{II}$ and $J_\perp$ as follows, remembering that they must be normalized properly to correspond to equations (10) and (11). For simplicity, assume that the angle $\lambda$, between the excitation and emission dipoles is zero, an accurate assumption for many fluorescent dyes. Then the functions $I_{II}$ must be normalized at t=0 to $\overrightarrow{3/5}$ and $I_\perp$ to $1/5$ since C=1 at t=0 for all species.

The parameters for 1, i.e., "bound" are found from measurements on the fluorescent ligand in the presence of varying concentrations of receptor by an extrapolation when necessary. For 2, i.e., "free", measurements in the absence of receptor give the proper function. All four I functions must be normalized as stated above. These determinations are analogs of the polarization for bound and free as utilized in conventional steady state fluorescence polarization immunoassay. Measurements on the blank may be utilized in a number of alternative ways. The most obvious is to measure $J_{\|Blk}$ and $J_{\perp Blk}$ for the blank itself and set these equal to the summations in Equations (64) and (65), respectively. However, if the time-dependents shapes of $J_{\|Blk}$ and $J_{\perp Blk}$ vary from sample to sample only by a constant factor at every point then a normalized background procedure can be used.

Consider measurements on the blank alone.

$$J_{\|Blk}(t) = \sum_j M_j q_j I_{j\|}(t) \quad (66)$$

$$J_{\perp Blk}(t) = \sum_j M_j q_j I_{j\perp}(t) \quad (67)$$

From equations (10) and (11), again setting $\lambda = 0$, it can be seen since the C's=1 at t=0 that $$J_{\|Blk}(0) = \frac{3}{5} \sum_j M_j q_j \quad (68)$$

$$J_{\perp Blk}(0) = \frac{1}{5} \sum_j M_j q_j \quad (69)$$

Now assume arbitrarily that the J's can be expressed as the product of a time dependent and a time independent function and proceed to evaluate these:

$$J_{\|Blk}(t) = S\, G_\|(t) \quad (70)$$

$$J_{\perp Blk}(t) = S\, G_\perp(t) \quad (71)$$

Substituting equations (70) and (71) into (64) and (65), respectively gives:

$$J_\|(t) = M_1 q_1 I_{1\|}(t) + M_2 q_2 I_{2\|}(t) + S\, G_\|(t) \quad (72)$$

$$J_\perp(t) = M_1 q_1 I_{1\perp}(t) + M_2 q_2 I_{2\perp}(t) + S\, G_\perp(t) \quad (73)$$

If S is set equal to $\Sigma M_j q_j$ then S is the rate of emission of energy (at zero time) from the background.

Having set $S = \Sigma M_j q_j$ enables the evaluation of the G's since $$G_\|(0) = \frac{3}{5} \text{ and} \quad (74)$$

$$G_\perp(0) = \frac{1}{5} \quad (75)$$

These are the values to which $G_\|$ and $G_\perp$ must be extrapolated using experimental data on the blank while the quantity S gives a measure of background/signal. The G's in turn can be calculated from molecular parameters since $$G_\|(t) = \frac{\sum_j M_j q_j I_{j\|}(t)}{\sum_j M_j q_j} \quad (76)$$

$$G_\perp(t) = \frac{\sum_j M_j q_j I_{j\perp}(t)}{\sum_j M_j q_j} \quad (77)$$

The procedures outlined above make it possible to interpret experimental values of $J_\|(t)$ and $J_{195}(t)$ from mixtures of several fluorescent species which may have similar excitation and emission properties but differ in decay time and/or rotary brownian motion. This interpretation is accomplished without resorting to the formidable and uncertain task of attempting to resolve the sums of several exponentials as are involved in the function "C" of equations (10) and (11) and without being forced to assume some excessively simplified model such as sphere or ellipsoid of revolution for the molecules in question. Such models have almost universally been assumed in the past in order to interpret rotation-dependent functions of transient-state fluorescence such as the anisotropy. It is precisely these difficulties and limitations that have impeded progress in the use of transient-state fluorescence. The approaches given here make transient state measurements generally useful for a wide variety of assays or other purposes.

In an immunoassay the total concentration, $M_T$, of fluorescent labeled ligand is known and if only one type of binding is present, $M_1 + M_2 = M_T$. For simplicity in the following, assume that $q_1 = q_2 = 1$. It should be noted that the generalization of the following treatment to multiple types of binding or to situations where quenching or enhancement occurs on binding is straightforward and obvious. With the assumptions above:

$$J_\| = M_1 I_{1\|} + (M_T - M_1) I_{2\|} + S\, G_\| \quad (78)$$

$$J_\perp = M_1 I_{1\perp} + (M_T - M_1) I_{2\perp} + S\, G_\perp \quad (79)$$

In equations (78) and (79) $S\, G_\|$ and $S\, G_\perp$ can be replaced by their equals, $$\sum_j M_j q_j I_{j\|} \text{ and } \sum_j M_j q_j I_{j\perp}$$

if desired.

Combination of equations (78) and (79) with the elimination of S yields an expression for $M_1$, the "bound" concentration in terms of experimentally measureable quantities in an assay.

$$M_1 = \frac{J_\perp G_\| - J_\| G_\perp + M_T(G_\perp I_{2\|} - G_\| I_{2\perp})}{G_\perp(I_{2\|} - I_{1\|}) - G_\|(I_{2\perp} - I_{1\perp})} \; ; \quad (q_1 = q_2 = 1) \quad (80)$$

Equation (80) is the expression for $M_1$, which results from the "normalized background" analysis if $q_1 = q_2 = 1$.

If it is desired to measure and utilize the intensity of background or blank simply by deducting it from that of the sample the J's can be written:

$$J_\| = M_1 q_1 I_{1\|} + (M_T - M_1) q_2 I_{2\|} + B_\| \quad (81)$$

$$J_\perp = M_1 q_1 I_{1\perp} + (M_T - M_1) q_2 I_{2\perp} + B_\perp \quad (82)$$

From equations (81) and (82) the expression for $M_1$ is:

$$M_1 = \frac{I_{2\|}(J_\perp - B_\perp) - I_{2\perp}(J_\| - B_\|)}{I_{2\|} I_{1\perp} - I_{1\|} I_{2\perp}} \; ; \quad (q_1 = q_2 = 1) \quad (83)$$

Equations (80) and (83) imply a computation of $M_1$ at one particular time, t, with all the functions evaluated for that value of t.

In equation (80) only the time dependent form of the blank is needed while the equation (83) the relative intensity on the same scale as that for $J_{\parallel}$ and $J_{\perp}$ is required.

If $q_1 \neq q_2$ then analogs of equations (80) and (83) are obtained:

$$J_{\parallel} = M_1 q_1 I_{1\parallel} + M_2 q_2 I_{2\parallel} + SG_{\parallel} \qquad (84)$$

$$J_{\perp} = M_1 q_1 I_{1\perp} + M_2 q_2 I_{2\perp} + SG_{\perp} \qquad (85)$$

Eliminating S and solving for $M_1$ gives:

$$M_1 = \frac{J_{\perp} G_{\parallel} - J_{\parallel} G_{\perp} + M_T q_2 (G_{\perp} I_{2\parallel} - G_{\parallel} I_{2\perp})}{G_{\perp}(q_2 I_{2\parallel} - q_1 I_{1\parallel}) - G_{\parallel}(q_2 I_{2\perp} - q_1 I_{1\perp})} \qquad (86)$$

From equations (81) and (82), $$M_1 = \frac{M_T[I_{2\parallel}(J_{\perp} - B_{\perp}) - I_{2\perp}(J_{\parallel} - B_{\parallel})]}{(J_{\parallel} - B_{\parallel})(I_{1\perp}[q_1/q_2] - I_{2\perp}) - (J_{\perp} - B_{\perp})(I_{1\parallel}[q_1/q_2] - I_{2\parallel})} \qquad (87)$$

The quantity $J_{\parallel} - J_{\perp}$ can be used to obtain $M_1$ by combining equations (81) and (82) with $q_1 = q_2 = 1$:

$$M_1 = \frac{(J_{\parallel} - J_{\perp}) - (B_{\parallel} - B_{\perp}) - M_T(I_{2\parallel} - I_{2\perp})}{(I_{1\parallel} - I_{1\perp}) - (I_{2\parallel} - I_{2\perp})} \;;\; (q_1 = q_2 = 1) \qquad (88)$$

$M_1$ can be obtained as an analog of equation (83) in which $M_T$ is not eliminated.

$$M_1 = \frac{J_{\perp}[M_T I_{2\parallel} + B_{\parallel}] - J_{\parallel}[M_T I_{2\perp} + B_{\perp}]}{J_{\parallel}[I_{1\perp} - I_{2\perp}] - J_{\perp}[I_{1\parallel} - I_{2\parallel}]} \;;\; (q_1 = q_2 = 1) \qquad (89)$$

Equation (81) can be solved for $M_1$ directly $$M_1 = \frac{J_{\parallel} - M_T I_{2\parallel} - B_{\parallel}}{I_{1\parallel} - I_{2\parallel}} \;;\; (q_1 = q_2 = 1) \qquad (90)$$

Equation (82) can be similarly solved:

$$M_1 = \frac{J_{\perp} - M_T I_{2\perp} - B_{\perp}}{I_{1\perp} - I_{2\perp}} \;;\; (q_1 = q_2 = 1) \qquad (91)$$

If $M_T$ is not eliminated and $q_1 \neq q_2$ then analogs of equations (90) and (91) are obtained:

$$M_1 = \frac{J_{\parallel} - M_T q_2 I_{2\parallel} - B_{\parallel}}{q_1 I_{1\parallel} - q_2 I_{2\parallel}} \qquad (92)$$

and $$M_1 = \frac{J_{\perp} - M_T q_2 I_{2\perp} - B_{\perp}}{q_1 I_{1\perp} - q_2 I_{2\perp}} \qquad (93)$$

The quantity $\Delta J_{EX} \equiv (J_{\parallel} - B_{\parallel}) - (J_{\perp} - B_{\perp})$ as a measured parameter gives:

$$M_1 = \frac{\Delta J_{EX} - M_T q_2 (I_{2\parallel} - I_{2\perp})}{q_1(I_{1\parallel} - I_{1\perp}) + q_2(I_{2\perp} - I_{2\parallel})} \qquad (94)$$

In equations (95) through (134) below, $q_1 = q_2 = 1$.
The ratio $J_{\parallel}/J_{\perp}$ inverse can be used as a parameter $$M_1 = \frac{\frac{J_{\parallel}}{J_{\perp}}[M_T I_{2\perp} + B_{\perp}] - M_T I_{2\parallel} - B_{\parallel}}{\frac{J_{\parallel}}{J_{\perp}}[I_{2\perp} - I_{1\perp}] + [I_{1\parallel} - I_{2\parallel}]} \qquad (95)$$

$$M_1 = \frac{\frac{J_{\perp}}{J_{\parallel}}[M_T I_{2\parallel} + B_{\parallel}] - M_T I_{2\perp} - B_{\perp}}{\frac{J_{\perp}}{J_{\parallel}}[I_{2\parallel} - I_{1\parallel}] + [I_{1\perp} - I_{2\perp}]} \qquad (96)$$

Data on the blank may be used in the form $B_{\perp}/B_{\parallel}$ or its inverse.

$$M_1 = \frac{J_{\perp} - M_T I_{2\perp} + \frac{B_{\perp}}{B_{\parallel}}[M_T I_{2\parallel} - J_{\parallel}]}{I_{1\perp} - I_{2\perp} + \frac{B_{\perp}}{B_{\parallel}}[I_{2\parallel} - I_{1\parallel}]} \qquad (97)$$

In some instances, e.g., in separation type assays, only the total fluorescent ligand concentration need be determined. In these cases variables such as $J_{\parallel} + 2J_{\perp}$ and $J_{\parallel} + J_{\perp}$ suffice.

$$M_T = \frac{(J_{\parallel} - B_{\parallel})(I_{1,\perp} - I_{2,\perp}) - (J_{\perp} - B_{\perp})(I_{1,\parallel} - I_{2,\parallel})}{I_{2,\parallel}(I_{1,\perp} - I_{2,\perp}) - I_{2,\perp}(I_{1,\parallel} - I_{2,\parallel})} \qquad (98)$$

$$M_T = \frac{(J_{\parallel} + 2J_{\perp}) - (B_{\parallel} + 2B_{\perp})}{I_{1,\parallel} + 2I_{1,\perp}} \qquad (99)$$

Note that equation (99) is simply a restatement in our notation that the "total" intensity is proportional to concentration.

In our methodology the use of polarization or anistropy is unnecessary but these quantities may be used if desired.

The time dependent polarization can be defined on the basis of excess fluorescence in the normal way:

$$P_F = \frac{(\Delta J_{\parallel} - \Delta J_{\perp})}{(\Delta J_{\parallel} + \Delta J_{\perp})} \qquad (100)$$

The ratio of bound/free is found to be, after eliminating $M_T$.

$$\frac{M_1}{M_2} = \frac{I_{2\parallel}(1 - p_F) - I_{2\perp}(1 + P_F)}{I_{1\perp}(1 + p_F) - I_{1\parallel}(1 - P_F)} \qquad (101)$$

An alternative form also based upon $P_F$ is:

$$M_1 = \frac{M_T(I_{2\parallel} - I_{2\perp}) - P_F M_T(I_{2\parallel} + I_{2\perp})}{P_F|I_{1\parallel} - I_{2\parallel} + I_{1\perp} - I_{2\perp}| - |I_{1\parallel} - I_{2\parallel} - I_{1\perp} + I_{2\perp}|} \qquad (102)$$

A different definition of the polarization can be made in terms of total instead of excess intensities:

$$P_S = \frac{J_{\parallel} - J_{\perp}}{J_{\parallel} + J_{\perp}} \qquad (103)$$

$M_1$ in terms of $P_S$ is found to be:

$$M_1 = \frac{M_T\{I_{2\parallel} - I_{2\perp} - P_S(I_{2\parallel} + I_{2\perp})\} - P_S\{B_{\parallel} + B_{\perp}\} + B_{\parallel} - B_{\perp}}{P_S\{I_{1\parallel} - I_{2\parallel} + I_{1\perp} - I_{2\perp}\} - \{I_{1\parallel} - I_{2\parallel} - I_{1\perp} + I_{2\perp}\}} \qquad (104)$$

Similar relationships can be obtained for the anisotropy defined in various ways. Defined in terms of the excess intensities $$An_F = \frac{(J_{\parallel} - B_{\parallel}) - (J_{\perp} - B_{\perp})}{(J_{\parallel} - B_{\parallel}) + 2(J_{\perp} - B_{\perp})} \qquad (105)$$

The expression for $M_1$ is found to be:

$$M_1 = \frac{M_T[I_{2\parallel} - I_{2\perp} - An_F(I_{2\parallel} + 2I_{2\perp})]}{An_F[I_{1\parallel} - I_{2\parallel} + 2I_{1\perp} - 2I_{2\perp}] + I_{2\parallel} - I_{1\parallel} + I_{1\perp} - I_{2\perp}} \qquad (106)$$

If the anisotropy is defined as $$An_S = \frac{J_\| - J_\perp}{J_\| + 2J_\perp} \quad (107)$$

The expression for $M_1$ is:

$$M_1 = \frac{-An_s[M_T(I_{2\|} + 2I_{2\perp}) + B_\| + 2B_\perp] + M_T[I_{2\|} - I_{2\perp}] + B_\| - B_\perp}{An_s[I_{1\|} - I_{2\|} + 2I_{1\perp} - 2I_{2\perp}] - [I_{1\|} - I_{1\perp} - I_{2\|} + I_{2\perp}]} \quad (108)$$

Anisotropies (and polarizations) can be used in still a different way in which separate anisotropies are measured for the complete solution and for the blank. Anisotropies are not additive functions but the proper means for combining them can be seen easily as follows: Weight each anisotropy by the fraction of the total rate of the emission of energy it represents and add the products.

The various anisotropies are:

$$An_S = \frac{J_\| - J_\perp}{J_\| + 2J_\perp} \quad (109)$$

$$An_B = \frac{B_\| - B_\perp}{B_\| + 2B_\perp} \quad (110)$$

and $$An_F = \frac{(J_\| - B_\|) - (J_\perp - B_\perp)}{(J_\| - B_\|) + 2(J_\perp - B_\perp)} \quad (111)$$

$$\left[\frac{B_\| - B_\perp}{B_\| + 2B_\perp}\right]\left[\frac{B_\| + 2B_\perp}{J_\| + 2J_\perp}\right] + \quad (112)$$

$$\left[\frac{(J_\| - B_\|) - (J_\perp - B_\perp)}{(J_\| - B_\|) + 2(J_\perp - B_\perp)}\right]\left[\frac{(J_\| - B_\|) + 2(J_\perp - B_\perp)}{J_\| + 2J_\perp}\right] = \frac{J_\| - J_\perp}{J_\| + 2J_\perp} = An_s$$

Thus the anisotropy of a mixture is related to the anisotropies of the individual constituents or groups of constituents by summing the anisotropies weighted in each case by the fraction of the total rate of emission of energy represented by that constituent or group of constituents, e.g. bound and free together or all the constituents of the blank together.

By expressing $An_F$ in terms of concentrations and I functions from equations (81) and (82) an expression for M (bound) is found.

$$A_{nF} = \frac{M_1 I_{1\|} + M_2 I_{2\|} - (M_1 I_{1\perp} + M_2 I_{2\perp})}{M_1 I_{1\|} + M_2 I_{2\|} + 2(M_1 I_{1\perp} + M_2 I_{2\perp})} \quad (113)$$

From equation (112)

$$An_s = An_F \left[\frac{[M_1 I_{1\|} + M_2 I_{2\|} + 2(M_1 I_{1\perp} + M_2 I_{2\perp})]}{J_\| + 2J_\perp}\right] + An_B\left[\frac{B_\| + 2B_\perp}{J_\| + 2J_\perp}\right] \quad (114)$$

Solving for $M_1$, gives:

$$M_1 = \frac{An_s(J_\| + 2J_\perp) - An_B(B_\| + 2B_\perp) - M_T(I_{2\|} - I_{2\perp})}{I_{1\|} - I_{2\|} - I_{1\perp} + I_{2\perp}} \quad (115)$$

Polarizations also are not additive functions, but may be combined as for anisotropies. In the case of polarizations the weighting factor is the fractional contribution to the total of the quantity $J_\| + J_\perp$.

These polarizations can be defined as:

$$P_S = \frac{J_\| - J_\perp}{J_\| + J_\perp} \quad (116)$$

$$P_B = \frac{B_\| - B_\perp}{B_\| + B_\perp} \quad (117)$$

$$P_F = \frac{(J_\| - B_\|) - (J_\perp - B_\perp)}{(J_\| - B_\|) + (J_\perp - B_\perp)} \quad (118)$$

A derivation analogous to that for equation (115) gives:

$$M_1 = \frac{P_S(J_\| + J_\perp) - P_B(B_\| + B_\perp) - M_T(I_{2'\|} - I_{2'\perp})}{I_{1'\|} - I_{2'\|} - I_{1'\perp} + I_{2'\perp}} \quad (119)$$

Analogs of equations (115) and (119) giving $M_1/M_2$ instead of M, are easily derivable.

As has been emphasized above anisotropies and polarizations are not additive but can be combined in ways we have shown. However, on a totally empirical approach the polarization of a blank could be simply subtracted from that of the sample to obtain a difference related to binding as follows:

From equations (116) and (117) take the difference $P_S - P_B$ and combine this difference with equations (81) and (82). The result for $M_1$ is:

$$M_1 = \quad (120)$$

$$\frac{(B_\| + B_\perp)\{M_T(I_{2\|} - I_{2\perp}) + B_\| - B_\perp - (P_S - P_B)(M_T[I_{2\|} + I_{2\perp}] + B_\| + B_\perp)\} - (B_\| - B_\perp)(M_T[I_{2\|} + I_{2\perp}] + B_\| + B_\perp)}{(B_\| + B_\perp)\{(I_{1\|} - I_{2\|} + I_{1\perp} - I_{2\perp})(P_S - P_B) - (I_{1\|} - I_{2\|} - I_{1\perp} + I_{2\perp})\} + (B_\| - B_\perp)(I_{1\|} - I_{2\|} + I_{1\perp} - I_{2\perp})}$$

In the foregoing treatment we have assumed that the experimental data consists of values of J's measured at discrete times during the decay curve. If instead, only the time integral of intensity over a time window is accessible a different approach can be taken. It may be noted that the integrated intensity is a simpler quantity to obtain and permits a simpler type of instrumentation to be used.

Equations (81) and (82) can be written ($q_1 = q_2 = 1$)

$$J_\|(t) = M_1 I_{1\|}(t) + M_2 I_{2\|}(t) + B_\|(t) \quad (121)$$

$$J_\perp(t) = M_1 I_{1\perp}(t) + M_2 I_{2\perp}(t) + B_\perp(t) \quad (122)$$

After integration over a time window from $t_A$ to $t_B$, $$\int_{t_A}^{t_B} J_\|(t)dt = M_1 \int_{t_A}^{t_B} I_{1'\|}(t)dt + M_2 \int_{t_A}^{t_B} I_{2'\|}(t)dt + \int_{t_A}^{t_B} B_\|(t)dt \quad (123)$$

$$\int_{t_A}^{t_B} J_\perp(t)dt = M_1 \int_{t_A}^{t_B} I_{1\perp}(t)dt + M_2 \int_{t_A}^{t_B} I_{2'\perp}(t)dt + \int_{t_A}^{t_B} B_\perp(t)dt \quad (124)$$

In equations (123) and (124) dropping t's and the limits of integration the integrals $\int J_\| dt$ and $\int J_\perp dt$, $\int B_\| dt$ and $\int B_\perp dt$ are determined for each experiment or assay. The integrals $\int I_{1\|} dt$, $\int I_{2\|} dt$, $\int I_{1\perp} dt$ and $\int I_{2\perp} dt$ are determined separately as parameters for fully bound or free forms of the fluorescent probe. Expressions for $M_1$ (bound) in terms of these integrals can be written as:

$$M_1 = \frac{\int J_\| dt - M_T \int I_{2\|} dt - \int B_\| dt}{\int I_{1\|} dt - \int I_{2\|} dt} \quad (125)$$

-continued or $$M_1 = \frac{\int J_\perp dt - M_T \int I_{2\perp} dt - \int B_\perp dt}{\int I_{1\perp} dt - \int I_{2\perp} dt} \quad (126)$$

Analogs of anisotropy, polarization or various combinations of ratios or differences may be used to obtain $M_1$. One example is:

$$\frac{\int J_\| dt - \int B_\| dt}{\int J_\perp dt - \int B_\perp dt}$$

abbreviated as LXRX, as the experimentally determined quantity in an assay.

$$M_1 = \frac{M_T[\int I_{2\|} dt - [LXRX]\int I_{2\perp} dt]}{[\int I_{1\perp} dt - \int I_{2\perp} dt][LXRX] - \int I_{1\|} dt + \int I_{2\|}} \quad (127)$$

The quantity $M_2$ can be eliminated from equations (123) and (124) resulting in $$M_1 = \frac{\{\int I_{2\|} dt\}\{\int B_\perp dt - \int J_\perp dt\} + \{\int I_{2\perp} dt\}\{\int J_\| dt - \int B_\| dt\}}{\{\int I_{2\perp} dt\}\{\int I_{1\|} dt - \int I_{2\|} dt\} - \{\int I_{2\|} dt\}\{\int I_{1\perp} dt - \int I_{2\perp} dt\}} \quad (128)$$

Linear combinations of $\int J_\| dt$ and $\int J_\perp dt$ can be used as parameters. Addition of the two integrals gives the following expression for $M_1$.

$$M_1 = \frac{\int I_\| dt + \int I_\perp dt - \int B_\| dt - \int B_\perp dt - M_T[\int I_{2\|} dt + \int I_{2\perp} dt]}{\int I_{1\|} dt + \int I_{1\perp} dt - \int I_{2\|} dt - \int I_{2\perp} dt} \quad (129)$$

An analog of the polarization, $IP_S$ equal to $$\frac{\int J_\| dt - \int J_\perp dt}{\int J_\| dt + \int J_\perp dt}$$

gives an expression for $M_1$ as $$M_1 = \frac{M_T[\int I_{2\|} dt - \int I_{2\perp} dt] + \int B_\| dt - \int B_\perp dt - IP_S}{IP_S[\int I_{1\|} dt - \int I_{2\|} dt + \int I_{1\perp} dt - \int I_{2\perp} dt] -} \\ \frac{\{M_T(\int I_{2\|} dt + \int I_{2\perp} dt) + \int B_\| dt + \int B_\perp dt\}}{[\int I_{1\|} dt + \int I_{2\|} dt + \int I_{1\perp} dt - \int I_{2\perp} dt]} \quad (130)$$

The analog of polarization can be based upon "excess integrated intensities":

$$IP_F = \frac{\int J_\| dt - \int B_\| dt - \int J_\perp dt + \int B_\perp dt}{\int J_\| dt - \int B_\| dt + \int J_\perp dt - \int B_\perp dt} \quad (131)$$

The expression for $M_S$ containing this parameter is:

$$M_1 = \frac{M_T\{\int I_{2\|} dt - \int I_{2\perp} dt - IP_F[\int I_{2\|} dt + \int I_{2\perp} dt]\}}{IP_F\{\int I_{1\|} dt - \int I_{2\|} dt + \int I_{1\perp} dt - \int I_{2\perp} dt\} -} \\ [\int I_{1\|} dt + \int I_{2\|} dt + \int I_{1\perp} dt - \int I_{2\perp} dt] \quad (132)$$

The "anistropy" based upon excess integrated intensities is:

$$An_F = \frac{\int J_\| dt - \int B_\| dt - \int J_\perp dt + \int B_\perp dt}{\int J_\| dt - \int B_\| dt + 2[\int J_\perp dt - \int B_\perp dt]} \quad (133)$$

The corresponding expression for $M_1$ is:

$$M_1 = \frac{M_T\{\int I_{2\|} dt - \int I_{2\perp} dt - An_F[\int I_{2\|} dt + 2\int I_{2\perp} dt]\}}{An_F[\int I_{1\|} dt - \int I_{2\|} dt + 2\int I_{1\perp} dt - 2\int I_{2\perp} dt] -} \\ \int I_{1\|} dt + \int I_{2\|} dt + \int I_{1\perp} dt - \int I_{2\perp} dt \quad (134)$$

In order to compare transient state results with those of steady state measurements the basic differences between the two must be examined. Consider an idealized situation in which two identical samples of fluorescent material can be illuminated with the same intensity from a common source. The illumination is begun simultaneously and at some time later the illumination is cut off from one sample (A) and continued on the other (B). At the instant the light is cut off (zero time) the two samples must have identical fluorescence emissions and, if during the excitation time steady-state conditions have been established in both A and B then the zero time emission from A is the same as the steady-state emission from B.

A critical issue in the above experiment is to determine what period of illumination is needed to establish the steady-state, i.e., does a short flash a nanosecond or less in duration allow sufficient time to reach steady-state. The time required involves 1) the time required for excitation to the first excited singlet state, about $10^{-15}$ sec., 2) the time to reach the lowest vibrational level and the nuclear configuration of the excited state, about $10^{-12}$ sec. and 3) the time to establish a steady-state concentration of any triplet states. This last factor is probably not important in the present context since the probability of intersystem crossing is only a few percent during one lifetime and since any emission resulting is at a longer wavelength and hence, easily excluded. Accordingly, it seems likely that a steady-state would be established during a typical dye laser flash (~500 psec) and that the steady state emission will be the same as that observed at zero time in the flashed sample, provided that the flash is not sufficiently intense to seriously depopulate the ground state. This conclusion furnishes a basis for comparison of conventional fluorescence polarization and transient-state polarized fluorescence, particularly with respect to the sensitivity attainable in binding assays based upon the two methods.

As a basis for comparison, consider fluorescence polarization immunoassay (FPIA) which is carried out with constant illumination of the sample. The vertically polarized component, V, polarized in the direction of the exciting field and the horizontally polarized component, H, polarized in a direction perpendicular to the exciting field are measured separately for sample and blank.

It may be seen that $V_S$ and $H_S$ for the sample and $V_B$ and $H_B$ for the blank correspond to $J_{II}(0)$ $J_\perp(0)$ $B_{II}(0)$ and $B_\perp(0)$ in transient-state measurements. The usual equations for FPIA are:

$$V_S - V_B = \Delta V \quad (135)$$

$$H_S - H_B = \Delta H \quad (136)$$

$$p = \frac{\Delta V - \Delta H}{\Delta V + \Delta H} \quad (137)$$

$$\frac{M_1}{M_2} = \frac{Q_b}{Q_f} \left[ \frac{p - p_f}{p_b - p} \right] \quad (138)$$

$$MQ = \Delta V + \Delta H \quad (139)$$

In these equations Q is a "molar fluorescence", p the polarization with subscripts "b" and "f" indicating bound and free. In the following as above we assume, for simplicity only, that all Q's=1, then, $$\frac{M_1}{M_2} = \frac{p - p_f}{p_b - p} = \frac{M_1}{M_T - M_1} \quad (140)$$

and $$M_1 = \frac{M_T(p - p_f)}{(p_b - p_f)} \quad (141)$$

$$p = \frac{M_1 p_b + M_2 p_f}{M_T} \quad (142)$$

$$\frac{\Delta V}{\Delta H} = \frac{1+p}{1-p} \quad (143)$$

$$\Delta H = \frac{M_T}{2}(1-p) \quad (144)$$

$$\Delta V = \frac{M_T}{2}(1+p) \quad (145)$$

If the fluorescence background is S times the signal and is unpolarized (assumed for convenience)

$$V_B + H_B = S(\Delta V + \Delta H), \quad (146)$$

$$V_B = H_B = \frac{S}{2}(\Delta V + \Delta H) \quad (147)$$

The difference between Q used here and the q in transient-state equations should be noted. Combining equations (50) and (54) gives:

$$J_{i,\parallel}(0) + 2J_{i,\perp}(0) = M_i q_i \quad (148)$$

Equation (139) for one component is:

$$M_i Q_i = V_i + H_i \quad (149)$$

on the basis of the discussion above we would expect that:

$$V_i + H_i = J_{i,\parallel}(0) + J_{i,\perp}(0) = M_i Q_i \quad (150)$$

and $$V_i + 2H_i = J_{i,\parallel}(0) + 2J_{i,\perp}(0) = M_i q_i \quad (151)$$

Hence, in making a comparison of signal/background, i.e., the ratio of the signal from the fluorescent probe divided by that from the blank, if we assume for convenience that all the fluorescence is unpolarized, we have:

$$\frac{J_{i\parallel}(0) + 2J_{i\perp}(0)}{B_\parallel + 2B_\perp(0)} = \frac{V_i + H_i}{V_B + H_B} \quad (152)$$

APPLICATION OF THEORY TO NUMERICAL SIMULATIONS OF IMMUNOASSAYS

Application of equations (12) through (25) make it possible to calculate numerical values of C(t), equation (12) from assumed values of the molecular parameters $\lambda$, $D_\alpha$, $D_\beta$, $D_\gamma$, $\theta'$ and $\Phi'$. The values of $I_{\parallel}$ and $I_{\perp}$ can then be obtained by using an assumed value for k in equation (49). Values of $J_{i\parallel}$ and $J_{i\perp}$ are obtained from equations (55) and (56) and finally $J_{\parallel}$ and $J_{\perp}$ from equations (62) and (63) or (64) and (65). Values G and S (equations (70) through (77) are obtained from assumed properties of the background fluorescence.

As examples of these simulations some of the expressions for $M_1$ (cf. equations (80) through (134) were used to assess the expected accuracy in determinations of $M_1$ (bound) when a very large background fluorescence is present. In this set of simulations the values assumed for the various parameters were as follows:

| | M | k (sec$^{-1}$) | $D_\alpha$ (sec$^{-1}$) | $D_\beta$ (sec$^{-1}$) | $D_\gamma$ (sec$^{-1}$) |
|---|---|---|---|---|---|
| 1 (Bound) | 1 | 3E7 | 6E6 | 4E6 | 2E6 |
| 2 (Free) | 1 | 3E7 | 6E8 | 4E8 | 2E8 |
| 3 (Background) | 400 | 1E8 | 3E8 | 4E7 | 5E7 |

Assumed accuracy in the data is ±1% on $J_{\parallel}$, $J_{\perp}$, $G_{\parallel}$, $G_{\perp}$, $B_{\parallel}$ or $B_{\perp}$. Background/signal=200. All Q's=1. $\lambda$=0, $\theta'$=$\phi'$=45°. Decay times: Dye 33 nsec, background, 10 nsec. Twenty data points from one decay curve were used to calculate the average value and standard deviation for $M_1$.

NUMERICAL SIMULATIONS

| Equation | Program Name | Average Value of $M_1$ | Standard Deviation |
|---|---|---|---|
| 80 | POLM | 0.96 | 0.41 |
| 83 | BOLA | 0.99 | 0.35 |
| 88 | BOLD | 0.99 | 0.37 |
| 89 | BOLE | 1.00 | 0.38 |
| 90 | BOLB | 1.00 | 0.41 |
| 91 | BOLC | 1.06 | 0.78 |
| 95 | BOLF | 0.96 | 0.39 |
| 96 | BOLO | 1.01 | 0.36 |
| 97 | BOLP | 0.99 | 0.37 |
| 98 | BOLQ | 0.99 | 0.09 |
| 99 | BOLS | 0.99 | 0.12 |
| 101 | BOLL | 1.55 | 2.22 |
| 102 | BOLJ | 1.01 | 0.41 |
| 104 | BOLK | 0.97 | 0.40 |
| 106 | BOLI | 0.98 | 0.42 |
| 108 | BOLH | 1.02 | 0.41 |
| 120 | BOLM | 1.00 | 0.32 |
| 125 | FITW | 0.84 | 0.59 |
| 126 | FITW | 1.12 | 0.98 |
| 127 | FITWB | | |
| 129 | FITW | 0.98 | 0.64 |
| 130 | FITWC | | |
| 132 | FITWD | | |
| 134 | FITWE | | |

A set of simulations designed to make useful predictions on the detection of antibody to rubella, on the immunoassay of digoxin and on DNA hybridization reactions was carried out. For the rubella system, $D_\beta$ for the labeled peptide bound to antibody was set at 0.88 ×10$^7$ sec$^{-1}$ corresponding to a rotational relaxation time of 57 nsec for a spherical particle. The relaxation time of 57 nsec is the experimental value (P. Wahl, Biochimica et Biophysica Acta, 181, 373–380 (1969) measured for fluorescein labeled $\gamma$-globulin. The polarization of the free peptide is 0.040. This value was used in the Perrin equation taking $p_0$=0.5 and 5 nsec for the decay time of fluorescein. Again assuming spherical geometry D, the rotary brownian diffusion constant was found to be 4.6× 10$^8$sec$^{-1}$ which was taken as $D_\beta$ for the free form. In all cases the data were assumed to be accurate to ±1%; the decay time of the fluorescent label was set at 20 nsec with a background of 3.6 nsec, the experimentally measured value for the major component in human serum. The same parameters were assumed to hold also for the digoxin and DNA systems in the absence of actual data for these. The results of these simulations show average values of $M_1$ (bound) and its standard deviation as a function of the different magnitudes of assumed background fluorescence.

| System | Background/signal = $\frac{S}{2}$ | $M_1$ (avg.) (Theory = 1) | Std. deviation, I |
|---|---|---|---|
| Rubella | 300 | 1.00 | 0.08 |
| Digoxin | 600 | 1.01 | 0.09 |
| DNA | 3000 | 1.01 | 0.18 |

Thus it appears that any of these systems may be satisfactorily quantified by our transient-state methodology.

A third set of simulations was done to compare the behavior of transient-state polarized fluorescence assays with those done by conventional fluorescence polarization. The parameters for the two types of assays were interrelated by means of the Perrin equation for spheres:

$$\left[\frac{1}{p} - \frac{1}{3}\right] = \left[\frac{1}{p_o} - \frac{1}{3}\right]\left[1 + \frac{3\tau}{\rho}\right] \qquad (153)$$

in which p is the observed polarization, $p_o$ the limiting polarization (taken to be 0.5) to be found as T, the temperature divided by viscosity →0, τ is the decay time and ρ is the rotational relaxation time.

$M_1/M_2$ was taken as 1 and background/signal as 600. For the steady-state fluorescence polarization, $p_f$=0.040, $P_b$=0.410, ρ=5×10$^{-9}$ sec with ρ=1.097×10$^{-9}$ sec. For the transient-state simulation for the bound form $D_\alpha$=0.78× 10$^7$sec$^{-1}$, $D_\beta$=0.88×10$^7$ and Dγ=0.98×10$^7$, $D_\beta$ correspond to a sphere of relaxation time =57 nsec. τ was taken as 20 nsec. For the free form $D_\alpha$=4.5×10$^8$. $D_\beta$=4.60×10$^8$ and $D_\gamma$=4.7× 10$^8$. The comparison of the two methods is shown below for ten replicate determinations.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. A fluorometer for measuring a fluorescence emanating from particular fluorophore molecules initially in a specimen with a dye and subsequently in the specimen without the dye to identify at least one of the existence and the concentration of the particular fluorophore molecules in the specimen, including, first means for producing a burst of concentrated light energy having a turn-off time short compared to the decay time of the fluorescence from the particular fluorophore molecules and having sufficient energy to excite the particular fluorophore molecules, second means responsive to the burst of the concentrated light energy for directing the burst of the concentrated light energy initially toward the specimen with the dye and subsequently toward the specimen without the dye to produce a fluorescence, including the fluorescence emanating from the particular fluorophore molecules, initially from the specimen with the dye and subsequently from the specimen without the dye, third means responsive to the fluorescence from the specimen initially with the dye and from the specimen subsequently without the dye for detecting the fluorescence, fourth means coupled to the third means for obtaining a controlled operation of the third means during a particular time period having a beginning time and an ending time to enhance the detection of the signals representing the fluorescence emanating from the particular fluorophore molecules relative to the portion of the signals representing the remaining fluorescence, the beginning time of the time period being a first particular time after the burst of the concentrated energy and after the production of the fluorescence emanating from the particular fluorophore molecules and the ending time being a second particular time after the first particular time and during the production of the fluorescence from the particular fluorophore molecules, the burst of concentrated light energy occurring before the particular time period, and fifth means coupled to the first means, the third means, and the fourth means for timing the operation of the third means to sequence the detection of the fluorescence during the particular time after the burst of the concentrated energy fluorescence, and sixth means for processing the detection of the fluorescence from the specimen with the dye and the specimen without the dye to provide an indication of the fluorescence emanating from the particular fluorophore molecules.

2. A fluorometer as set forth in claim 1, including, means for scanning the specimen initially with the dye and subsequently the specimen without the dye to obtain a reproduction of the different positions on the specimen.

3. A fluorometer as set forth in claim 1 wherein the third means includes a photosensitive array for detecting the fluorescence emanating from a plurality of positions initially on the specimen with the dye and subsequently on the specimen without the dye and the second means includes an array control for scanning the photosensitive array to obtain a reproduction of the detected fluorescence at the different positions initially on the specimen with the dye and subsequently on the specimen without the dye.

4. A fluorometer for measuring a fluorescence emanating from particular fluorophore molecules initially in a specimen with a dye and subsequently in the specimen without the dye to identify at least one of the existence and the concentration of the particular fluorophore molecules in the specimen, including, first means for producing a burst of concentrated light having a sufficient energy to excite the particular fluorophore molecules, second means responsive to the burst of concentrated light energy for directing the concentrated light energy toward the specimen initially with the dye and subsequently toward the specimen without the dye to produce a fluorescence, including the fluorescence from the particular fluorophore molecules, from the specimen initially with the dye and subsequently from the specimen without the dye, and third means responsive to the fluorescence from the particular fluorophore molecules in the specimen initially with the dye and subsequently in the specimen without the dye for providing an indication of the particular fluorophore molecules in the specimen.

5. In a combination as set forth in claim 4, including, the third means being operative after the pulsing of the first means and for a particular time during the production of the fluorescence from the particular fluorophore molecules in the specimen initially with the dye and subsequently in the specimen without the dye to provide an indication of the particular fluorophore molecules in the specimen.

6. A fluorometer for measuring a fluorescence emanating from particular fluorophore molecules initially in a specimen with a dye and subsequently in the specimen without the dye to identify at least one of the existence and the concentration of the particular fluorophore molecules in the specimen, including, first means for producing pulses of light at a particular wavelength to obtain a fluorescence initially of the particular fluorophore molecules in the specimen with the dye and subsequently of the particular fluorophore molecules in the specimen without the dye, second means for directing the pulses of light at the particular wavelength initially to the specimen with the dye and subsequently to the specimen without the dye to obtain initially the fluorescence of the specimen with the dye and subsequently the fluorescence of the specimen without the dye, third means for determining the fluorescence initially from the specimen with the dye and subsequently from the specimen without the dye, and fourth means for eliminating the effects of the fluorescence from the specimen without the dye from the determination provided by the third means of the fluorescence from the specimen with the dye to indicate the particular fluorophore molecules in the specimen.

7. A fluorometer as set forth in claim 6, including, the specimen with the dye containing the dye, an antibody and an antigen and the specimen without the dye containing the antigen and the antibody, and the fourth means including data processing means for processing the determinations of the fluorescence in the specimen with the dye and without the dye to obtain a measurement of the fluorescence emanating from the particular fluorophore molecules in the specimen.

8. A fluorometer as set forth in claim 6 wherein the third means determines the fluorescence in a particular period of time from the initiation of the production of the fluorescence initially in the specimen with the dye and subsequently in the specimen without the dye and before the end of the fluorescence in the particular fluorophore molecules as a result of the pulses of light from the first means and wherein the fourth means eliminates the effects of the fluorescence in the particular time period of the fluorescence in the specimen without the dye from the determinations of the fluorescence in the particular time period of the fluorescence in the specimen with the dye.

9. A fluorometer for measuring a fluorescence emanating from particular fluorophore molecules in a specimen with a dye and subsequently in a specimen without the dye to identify at least one of the existence and the concentration of the particular fluorophore molecules in the specimen, including, first means for producing pulses of light at a particular wavelength to obtain a fluorescence initially of the specimen with the dye and a fluorescence subsequently of the specimen without the dye, second means for directing the pulses of light at the particular wavelength to the specimen to obtain initially a fluorescence of the specimen with the dye and subsequently a fluorescence of the specimen without the dye, third means for determining the fluorescence initially from the specimen with the dye and subsequently from the specimen without the dye, and fourth means for eliminating the effects of the fluorescence from the specimen without the dye from the determination of the fluorescence from the specimen with the dye.

10. A fluorometer for measuring a fluorescence emanating from particular fluorophore molecules initially in a specimen with a dye and subsequently in the specimen without the dye to identify at least one of the existence and the concentration of the particular fluorophore molecules in the specimen, including, first means for producing a burst of concentrated light energy having sufficient energy to excite the particular fluorophore molecules in the specimen, second means responsive to the burst of concentrated light energy for directing the burst of the concentrated light: energy initially toward the specimen with the dye and subsequently toward the specimen without the dye to produce a. fluorescence from the specimen, including the fluorescence from the particular fluorophore molecules, initially from the specimen with the dye and subsequently from the specimen without the dye, third means responsive to the fluorescence from the specimen, initially with the dye and subsequently without the dye, for detecting such fluorescence and for producing signals in accordance with such detection, fourth means coupled to the third means for obtaining a controlled operation of the third means during a particular time period to optimize the detection of the fluorescence from the particular fluorophore molecules during the particular time period initially for the specimen with the dye and subsequently for the specimen without the dye, the particular time period having a beginning time and an ending time to enhance the detection of the signals representing the fluorescence from the particular fluorophore molecules during the particular time period in the specimen with the dye, the beginning time and the ending time of the particular period occurring during the production of the fluorescence from the particular fluorophore molecules in the specimen with the dye as a result of the burst of the concentrated light energy, fifth means coupled to the first means, to the third means and to the fourth means for timing the operation of the third means to sequence the detection of the fluorescence during the particular time period from the specimen initially with the dye and from the specimen subsequently without the dye as a result of the production of the burst of concentrated light energy, sixth means responsive to the signals produced by the third means during the particular time period for analyzing the signals to enhance the portion of the signals representing the fluorescence from the particular fluorophore molecules in the specimen with the dye, and seventh means responsive to the signals from the sixth means for indicating at least one of the identity and the concentration of the fluorescence from the particular fluorophore molecules in the specimen.

11. A fluorometer as set forth in claim 10 wherein the seventh means provides an image of the fluorescence from the particular fluorophore molecules in the specimen.

12. A fluorometer as set forth in claim 10 wherein the specimen is disposed in a solution with the dye and such dye produces the fluorescence in response to the light directed in the burst to the solution and wherein the sixth means includes means for processing the signals from the third means for the specimen in the solution with the dye and for the specimen in the solution without the dye to enhance the indication of the fluorescence from the particular fluorophore molecules in the specimen.

13. A fluorometer as set forth in claim 10 wherein the specimen is disposed in a solution with other ingredients and such other ingredients produce a fluorescence in response to the light directed in the burst to the solution and wherein the light is directed initially to the specimen with the dye and subsequently to the specimen without the dye and wherein the specimen and the other ingredients produce the fluorescence initially in the specimen with the dye and wherein the sixth means includes eighth means for processing the signals from the third means to enhance the indication of at least one of the identity and the concentration of the fluorescence from the particular fluorophore molecules in the specimen.

14. A fluorometer for measuring a fluorescence emanating from particular fluorophore molecules in a particular one of an antibody and an antigen by providing a dye and by attaching the particular one of the antigen and the antibody to the dye and by disposing the combination of the dye and the particular one of the antigen and the antibody in a specimen with the other one of the antigen and the antibody to determine the combination of the other one of the antigen and the antibody with the combination of the dye and the particular one of the antigen and the antibody, first means for directing bursts of light energy at a particular wavelength to the specimen initially with the dye and subsequently without the dye to obtain a fluorescence of the antigen, the dye, the antibody, the combination of the antigen and the antibody, the combination of the dye with the particular one of the antigen and the antibody and the dye-antibody-antigen combination and to obtain a fluorescence of the antigen, the dye, the antibody, the combination of the antigen and the antibody, the combination of the dye with the particular one of the antigen and the antibody and the dye-antibody-antigen combination and a fluorescence subsequently of the antigen, the antibody and the combination of the antigen and the antibody, second means for detecting the fluorescence initially from the antigen, the dye, the antibody, the combination of the dye and the particular one of the antigen and the antibody and the dye-antibody-antigen combination and subsequently from the antigen, the antibody and the combination of the antigen and the antibody, and third means for processing the effects of the fluorescence from the antigen, the antibody, the dye, the combination of the antigen and the antibody and the combination of the dye and the particular one of the antigen and the antibody and the dye-antibody-antigen combination to obtain an indication of the fluorescence emanating from the particular fluorophore molecules in the antigen.

15. A fluorometer as set forth in claim 14 wherein the second means is operative after the bursts of the light energy to detect the fluorescence initially from the antigen, the dye, the antibody, the combination of the antigen and the antibody, the combination of the dye with particular one of the antigen and the antibody and the dye-antibody-antigen combination and subsequently from the antigen, the antibody and the combination of the antigen and the antibody only upon the occurrence of their fluorescence and only for a particular time thereafter, the particular time being less than the time for the occurrence of the fluorescence in the dye-antibody-antigen combination, and wherein the third means is operative to eliminate the effects, of the antigen, the dye, the antibody and the combination of the dye and the particular one of the antigen and the antibody from the detection by the second means only for the particular time after their fluorescence.

* * * * *

UNITED STATES PATENT AND TRADEMARK OFFICE
CERTIFICATE OF CORRECTION

PATENT NO. : 5,876,672
DATED : March 2, 1999
INVENTOR(S) : Walter B. Dandliker, et al.

It is certified that error appears in the above-identified patent and that said Letters Patent is hereby corrected as shown below:

Column 1, line 39, change "delay" two occurrences, to read --decay--.

Column 10, line 55, change "may be", to read --is--.

Column 13, line 30 change "(Zα,Zβ,Zγ)", to read --($Z_\alpha, Z_\beta, Z_\gamma$)--.

Column 13, line 32 change "+$Z_\beta$ + $Z_\beta$", to read --+$Z_\beta$ +$Z_\gamma$--.

Column 13, line 66 change "y$\alpha$", to read --$y_\alpha$--.

Column 26, line 51, change "181", to read --<u>181</u>--.

Column 27, at line 33, add the following omitted text:

--<u>Values for $M_1$ (Theory =- 1)</u>

| Transient-State Polarized Fluorescence (Eq.80) | Conventional Fluorescence Polarization (Eq.141) |
|---|---|
| 1.01 ± 0.09 | 8.89 ± 5.50 |
| 1.00 ± 0.08 | 11.80 ± 53.00 |
| 0.99 ± 0.07 | -10.00 ± 339.00 |
| 1.00 ± 0.09 | 21.40 ± 68.00 |
| 0.99 ± 0.08 | 6.05 ± 21.70 |
| 1.01 ± 0.06 | 3.07 ± 13.50 |
| 1.00 ± 0.07 | -3.96 ± 11.50 |
| 0.98 ± 0.10 | -16.80 ± 28.30 |
| 0.99 ± 0.08 | 4.42 ± 51.00 |
| 1.01 ± 0.07 | 15.30 ± 31.60 |
| Avg. 1.00 ± 0.08 | Avg. 3.13 ± 68.00 |

UNITED STATES PATENT AND TRADEMARK OFFICE
CERTIFICATE OF CORRECTION

PATENT NO.  : 5,876,672
DATED       : Mar. 2, 1999
INVENTOR(S) : Walter Beach Dandliker, et al.

It is certified that error appears in the above-identified patent and that said Letters Patent is hereby corrected as shown below:

It appears that transient-state fluorescence assays should have perhaps several hundred times the sensitivity of conventional fluorescence polarization, thus opening up many assays now done by other methods, e.g. separation methods, and also making it possible to quantitate DNA hybridization detectable by simple homogeneous assays.--

Front page, in the title, change "LUMINESCENE", to read --LUMINESCENCE--.

Column 1, line 2, in the title, change "LUMINESCENE", to read --LUMINESCENCE--.

Signed and Sealed this

Tenth Day of August, 1999

*Attest:*

Q. TODD DICKINSON